US012249431B2

(12) United States Patent
Del Pino Ruiz et al.

(10) Patent No.: US 12,249,431 B2
(45) Date of Patent: Mar. 11, 2025

(54) PREDICTIVE DATA ANALYSIS TECHNIQUES FOR OPTIMAL TRAVERSAL OF INFECTION NETWORKS

(71) Applicant: Optum Services (Ireland) Limited, Dublin (IE)

(72) Inventors: Vicente Rubén Del Pino Ruiz, Dublin (IE); Hendrik Kleine, Dublin (IE); Harutyun Shahumyan, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 592 days.

(21) Appl. No.: 17/110,965

(22) Filed: Dec. 3, 2020

(65) Prior Publication Data

US 2022/0115146 A1    Apr. 14, 2022

Related U.S. Application Data

(60) Provisional application No. 63/089,576, filed on Oct. 9, 2020.

(51) Int. Cl.
*G16H 50/80* (2018.01)
*G06Q 10/047* (2023.01)
(Continued)

(52) U.S. Cl.
CPC .......... *G16H 50/80* (2018.01); *G06Q 10/047* (2013.01); *G16H 40/20* (2018.01); *G16H 50/30* (2018.01); *G16H 50/70* (2018.01); *H04L 67/52* (2022.05)

(58) Field of Classification Search
CPC ........ G16H 50/80; G16H 50/30; G16H 40/20; G16H 50/70; G06Q 10/047; G06Q 50/265; G06Q 90/20; G16Q 50/265
See application file for complete search history.

(56) References Cited

U.S. PATENT DOCUMENTS 7,993,266 B2   8/2011   Colston, Jr. et al.
8,652,040 B2   2/2014   LeBoeuf et al.
(Continued)

OTHER PUBLICATIONS

Noakes et al., Mathematical models for assessing the role of airflow on the risk of airborne infection in hospital wards, Oct. 2009, The Royal Society Interface (Year: 2009).*
(Continued)

*Primary Examiner* — Karen A Hranek
(74) *Attorney, Agent, or Firm* — Alston & Bird LLP

(57) ABSTRACT

Solutions for more efficient and effective traversal of infection networks are disclosed. In one example, a method includes identifying a plurality of candidate traversal paths for the traversal agent object; for each candidate traversal path of the plurality of candidate traversal paths, determining a cross-node infectious encounter profile that defines one or more predicted infectious encounters for the traversal agent data object, determining a predicted total viral particle inhalation (VPI) measure for each predicted infectious encounter of the one or more predicted infectious encounters, and determining a path risk score based at least in part on each predicted total VPI measure for a predicted infectious encounter of the one or more predicted infectious encounters; determining the optimal traversal path based at least in part on each path risk score for a candidate traversal path of the plurality of candidate traversal paths; and performing one or more prediction-based actions based at least in part on the optimal traversal path.

16 Claims, 13 Drawing Sheets

Figure 1:
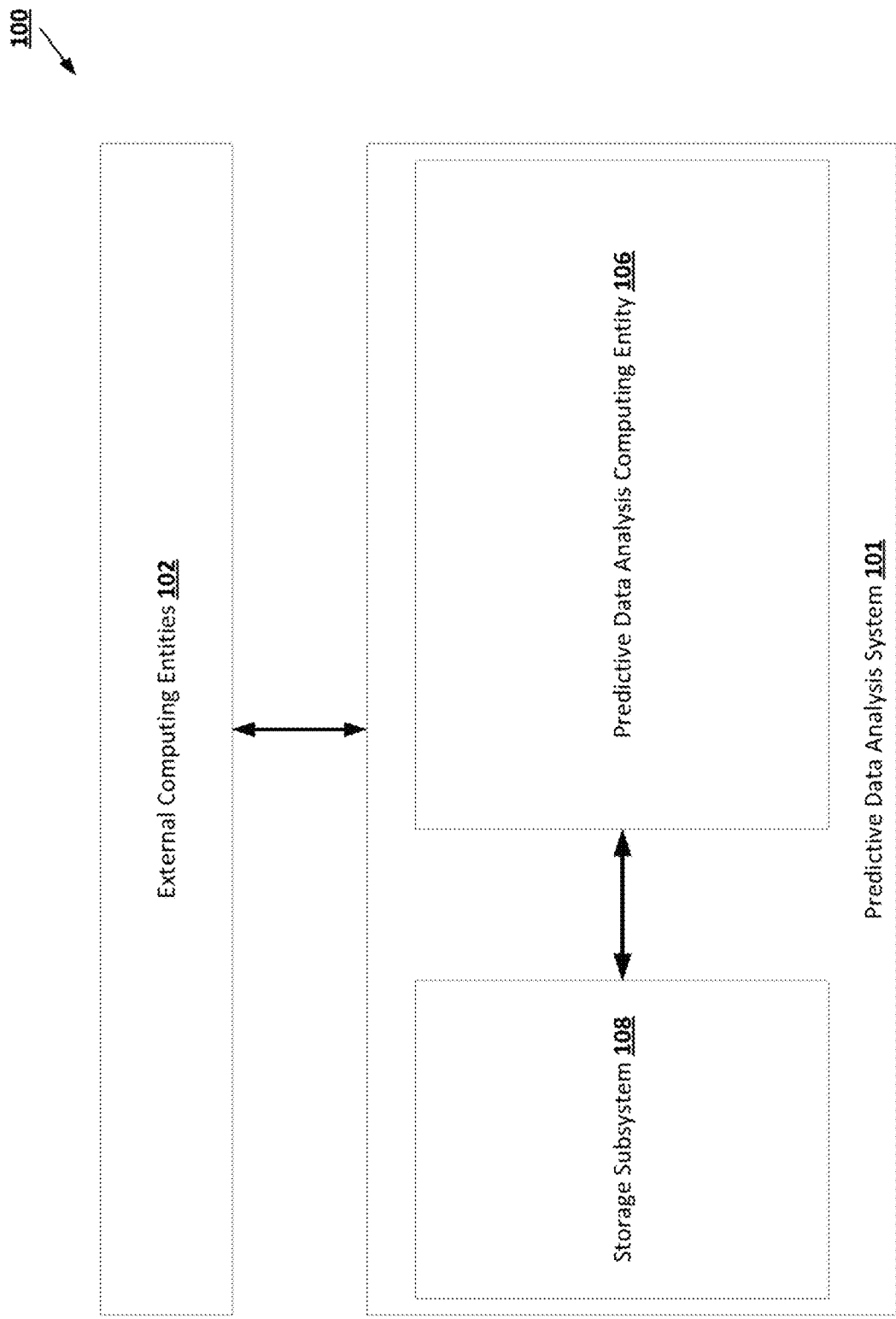

(51) Int. Cl.
*G16H 40/20* (2018.01)
*G16H 50/30* (2018.01)
*G16H 50/70* (2018.01)
*H04L 67/52* (2022.01)

(56) References Cited

U.S. PATENT DOCUMENTS

| | | | |
|---|---|---|---|
| 8,936,944 | B2 | 1/2015 | Peltz et al. |
| 9,075,909 | B2 | 7/2015 | Almogy et al. |
| 9,460,263 | B2 | 10/2016 | Holmes et al. |
| 9,546,874 | B2 * | 1/2017 | Compton ............. G01C 21/206 |
| 9,727,702 | B2 | 8/2017 | Kass-Hout et al. |
| 10,366,791 | B1 | 7/2019 | Thiagarajan et al. |
| 10,956,855 | B1 * | 3/2021 | Coughran ............. G06Q 10/047 |
| 2003/0204130 | A1 | 10/2003 | Colston, Jr. et al. |
| 2012/0112883 | A1 | 5/2012 | Wallace et al. |
| 2013/0318027 | A1 | 11/2013 | Almogy et al. |
| 2016/0132652 | A1 | 5/2016 | Chapman Bates et al. |
| 2016/0140830 | A1 | 5/2016 | Hathom |
| 2016/0314185 | A1 | 10/2016 | Buchanan et al. |
| 2017/0024531 | A1 * | 1/2017 | Malaviya ............... G16H 50/30 |
| 2017/0193792 | A1 * | 7/2017 | Bermudez Rodriguez ................... G08B 5/224 |
| 2017/0351831 | A1 * | 12/2017 | Cahan ................... G06T 11/206 |
| 2017/0352119 | A1 * | 12/2017 | Pittman ................. G16H 50/80 |
| 2018/0096544 | A1 * | 4/2018 | James ................... G07C 9/00896 |
| 2018/0225421 | A1 * | 8/2018 | Balasubramanian .. G06Q 50/01 |
| 2019/0333647 | A1 * | 10/2019 | Hoss ...................... G16H 50/80 |
| 2020/0176125 | A1 * | 6/2020 | Chatterjea ............. G16H 40/20 |
| 2020/0217677 | A1 * | 7/2020 | Wang ................... G01C 21/3461 |
| 2020/0335226 | A1 * | 10/2020 | Hara ...................... G16B 45/00 |
| 2021/0011443 | A1 * | 1/2021 | McNamara .......... F24F 11/0001 |
| 2021/0190504 | A1 * | 6/2021 | Hayes-Thakore ... G01C 21/206 |
| 2021/0257107 | A1 * | 8/2021 | Hassan ................. G16H 10/60 |
| 2021/0313075 | A1 * | 10/2021 | McNamara .......... G08B 21/182 |
| 2021/0358632 | A1 * | 11/2021 | Fazio ..................... G06F 16/75 |
| 2021/0407690 | A1 * | 12/2021 | Locke ................... H04L 63/126 |
| 2022/0028561 | A1 * | 1/2022 | Klasson ................. G06N 20/20 |
| 2022/0051807 | A1 * | 2/2022 | Subramanian ......... G16H 50/30 |
| 2022/0068499 | A1 * | 3/2022 | Tadesse ................. G16H 50/50 |
| 2022/0093275 | A1 * | 3/2022 | Sternberg ............... G16H 50/20 |
| 2022/0102012 | A1 * | 3/2022 | Son ........................ G16H 10/40 |
| 2022/0109949 | A1 * | 4/2022 | Alemi ................... H04W 4/025 |
| 2022/0136857 | A1 * | 5/2022 | Pompili ................. G16H 50/70 701/409 |
| 2022/0165433 | A1 * | 5/2022 | Schimmoller ......... G16H 50/50 |
| 2022/0170756 | A1 * | 6/2022 | Imtiyaz Shaikh ...... H04W 4/44 |

OTHER PUBLICATIONS

Buonanno et al., Estimation of airborne viral emission: quanta emission rate of SARS-COV-2 for infection risk assessment, Apr. 2020, medRxiv (Year: 2020).*

Mittal et al., A mathematical framework for estimating risk of airborne transmission of COVID-19 with application to face mask use and social distancing, Oct. 7, 2020, Physics of Fluids (Year: 2020).*

Chai, Modelling Spreading Process Induced by Agent Mobility in Complex Networks, Oct.-Dec. 2018, IEEE Transactions on Network Science and Engineering, vol. 5, No. 4 (Year: 2018).*

"Expert Reaction to Questions About COVID-19 and Viral Load," Science Media Centre, Mar. 24, 2020, (7 pages). [online]. [Retrieved from the Internet Feb. 10, 2021] URL: https://www.sciencemediacentre.org/expert-reaction-to-questions-about-covid-19-and-viral-load/.

"Public Health Guidance for Community-Related Exposure," Centers for Disease Control and Prevention, Dec. 3, 2020, (2 pages). [online]. [Retrieved from the Internet Feb. 10, 2021] URL: https://www.cdc.gov/coronavirus/2019-ncov/php/public-health-recommendations.html.

Asadi, Sima et al. "Aerosol Emission and Superemission During Human Speech Increase With Voice Loudness," Scientific Reports, vol. 9, No. 2348, Feb. 20, 2019, pp. 1-10. DOI: 10.1038/s41598-019-38808-z.

Bromage, Erin. "The Risks—Know Them—Avoid Them," May 20, 2020, (15 pages). [article, online]. [Retrieved from the Internet Feb. 10, 2021] URL: https://www.erinbromage.com/post/the-risks-know-them-avoid-them.

Cho, Hyunghoon et al. "Contact Tracing Mobile Apps For COVID-19: Privacy Considerations and Related Trade-Offs," arXiv preprint arXiv:2003.11511, Mar. 25, 2020, (12 pages).

Nishiura, Hiroshi et al. "Closed Environments Facilitate Secondary Transmission of Coronavirus Disease 2019 (COVID-19)," medRxiv preprint, Apr. 16, 2020, pp. 1-7. DOI: 10.1101/2020/02.28.20029272.

Qian, Hua et al. "Indoor Transmission of SARS-COV-2," medRxiv preprint, Apr. 7, 2020, pp. 1-22. DOI: 10.1101/2020.04.04.20053058.

Vazquez-Prokopec, Gonzalo M. et al. "Usefulness of Commercially Available GPS Data-Loggers for Tracking Human Movement and Exposure to Dengue Virus," International Journal of Health Geographics, vol. 8, No. 68, Nov. 30, 2009, pp. 1-11. DOI: 10.1186/1476-072X-8-68.

Vespignani, Alessandro et al. "Modelling COVID-19," Nature Reviews|Physics, vol. 2, Jun. 2020, pp. 279-281. DOI: 10.1038/s42254-020-0178-4.

Yan, Jing et al., "Infectious Virus in Exhaled Breath of Symptomatic Seasonal Influenza Cases From a College Community," Proceedings of the National Academy of Sciences of the United States of America, vol. 115, No. 5, Jan. 30, 2018, pp. 1081-1086. DOI:10.1073/pnas.1716561115.

* cited by examiner

| Resource | Information |
|---|---|
| Device ID | Identifier of the device generating the information. |
| Device Type | Type of device generating the information. |
| Device Location | Location of the device generating information or location generated by the device. |
| Creation Timestamp | Timestamp of when the location was collected. |
| Validity Duration | Time during which the location will be valid. |

FIG. 5

PREDICTIVE DATA ANALYSIS TECHNIQUES FOR OPTIMAL TRAVERSAL OF INFECTION NETWORKS

CROSS-REFERENCE TO RELATED APPLICATION(S)

The present application claims priority to the U.S. Provisional Patent Application No. 63/089,576, filed Oct. 9, 2020, which is incorporated by reference herein in its entirety.

BACKGROUND

Various embodiments of the present invention address technical challenges related to performing efficient and effective traversal of infection networks.

BRIEF SUMMARY

In general, embodiments of the present invention provide methods, apparatuses, systems, computing devices, computing entities, and/or the like for performing efficient and effective traversal of infection networks by using risk modeling techniques that use viral particle inhalation (VPI) measures and viral particle density (VPD) measures.

In accordance with one aspect, a method includes: identifying a plurality of candidate traversal paths for the traversal agent object; for each candidate traversal path of the plurality of candidate traversal paths, determining a cross-node infectious encounter profile that defines one or more predicted infectious encounters for the traversal agent data object, determining a predicted total viral particle inhalation (VPI) measure for each predicted infectious encounter of the one or more predicted infectious encounters, and determining a path risk score based at least in part on each predicted total VPI measure for a predicted infectious encounter of the one or more predicted infectious encounters; determining the optimal traversal path based at least in part on each path risk score for a candidate traversal path of the plurality of candidate traversal paths; and performing one or more prediction-based actions based at least in part on the optimal traversal path.

In accordance with another aspect, an apparatus comprising at least one processor and at least one memory including program code, the at least one memory and the program code configured to, with the processor, cause the apparatus to at least: identify a plurality of candidate traversal paths for the traversal agent object; for each candidate traversal path of the plurality of candidate traversal paths, determine a cross-node infectious encounter profile that defines one or more predicted infectious encounters for the traversal agent data object, determine a predicted total viral particle inhalation (VPI) measure for each predicted infectious encounter of the one or more predicted infectious encounters, and determine a path risk score based at least in part on each predicted total VPI measure for a predicted infectious encounter of the one or more predicted infectious encounters; determine the optimal traversal path based at least in part on each path risk score for a candidate traversal path of the plurality of candidate traversal paths; and perform one or more prediction-based actions based at least in part on the optimal traversal path.

In accordance with yet another aspect, a computer program product computer program comprising at least one non-transitory computer-readable storage medium having computer-readable program code portions stored therein, the computer-readable program code portions configured to: identify a plurality of candidate traversal paths for the traversal agent object; for each candidate traversal path of the plurality of candidate traversal paths, determine a cross-node infectious encounter profile that defines one or more predicted infectious encounters for the traversal agent data object, determine a predicted total viral particle inhalation (VPI) measure for each predicted infectious encounter of the one or more predicted infectious encounters, and determine a path risk score based at least in part on each predicted total VPI measure for a predicted infectious encounter of the one or more predicted infectious encounters; determine the optimal traversal path based at least in part on each path risk score for a candidate traversal path of the plurality of candidate traversal paths; and perform one or more prediction-based actions based at least in part on the optimal traversal path.

BRIEF DESCRIPTION OF THE DRAWINGS

Having thus described the invention in general terms, reference will now be made to the accompanying drawings, which are not necessarily drawn to scale, and wherein:

FIG. 1 provides an exemplary overview of a system that can be used to practice embodiments of the present invention;

FIG. 2 provides an example predictive data analysis computing entity in accordance with some embodiments discussed herein;

FIG. 3 provides an example external computing entity in accordance with some embodiments discussed herein;

FIG. 4 is a flowchart diagram of an example process for determining an optimal traversal path within a traversal network in accordance with some embodiments discussed herein;

FIG. 5 provides an operational example of a data schema for a location data object in accordance with some embodiments discussed herein;

FIG. 6 provides an operational example of a traversal network in accordance with some embodiments discussed herein;

FIGS. 7A-7B provide operational examples of two candidate traversal paths in accordance with some embodiments discussed herein;

FIG. 8 provides an operational example of a node visitation recommendation data object in accordance with some embodiments discussed herein;

FIG. 9 provides an operational example of detecting a predicted infectious encounter in accordance with some embodiments discussed herein; profile FIGS. 10-11 provide operational examples of two prediction output user interfaces in accordance with some embodiments discussed herein; and FIG. 12 is a flowchart diagram of an example process for determining an optimal traversal path list in accordance with some embodiments discussed herein.

DETAILED DESCRIPTION

Various embodiments of the present invention are described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

Overview and Technical Advantages

Various embodiments of the present invention provide techniques for efficiently and effectively traversing an infection network by performing graph-based inferences about agent co-visitation as well as agent visitation of high-risk areas before performing computationally resource-intensive infection risk modeling operations. The graph-based techniques introduced herein enable substantially shrinking the number of risk modeling iterations that need to be performed as part of generating traversal paths across traversal networks, as temporal path occurrence information about traversal of various agents are used to focus the focus of the risk modeling analysis on identified path co-occurrences, rather than on all possible pair of traversal paths. Because of this, various embodiments of the present invention are able to perform network-wide infection risk modeling in a computationally efficient manner and by using fewer processing cycles. In this way, various embodiments of the present invention improve computational efficiency of performing network-wide risk modeling and disclose innovative and technologically advantageous solutions for performing faster network-wide risk modeling, a feature that in turn enables performing network-wide risk modeling operations in a real-time or near-real-time manner.

An example application of various embodiments of the present invention relates to exposure tracking for infection/viral diseases. In times of pandemic or in highly contagious environments, it is critical to track any exposure and transmission among healthcare professionals. There are multiple approaches used in healthcare and research environments that relate to enforcing the authentication protocols needed to access to any risk environment. The information gathered is processed in a central location and used track the access to specific locations by healthcare professionals or patients. However, none the existing solutions for this problem leverage the information gathered to build a risk model to detect the probability of being infected after an exposure or to improve layout of facilities. Various embodiments of the present invention solve the above-described shortcomings by combining the information generated by wireless devices, mobile devices, or any hardware implemented to control access in the building to track staff across all the rooms and aisles. This makes the invention a passive system which does not need any manual intervention and tracks all the different areas where members and professionals may interact protecting their privacy. With the information gathered, a statistical model is generated to calculate the risk and probability of being infected across various candidate traversal paths. In some embodiments, the noted statistical model is also able to generate a set of safe paths with a low probability of risk of infection, where the noted paths are customized for each specific employee in healthcare facilities.

Various embodiments of the present invention propose a method to systematically and proactively track the interaction and movements of people in a building. The method is composed of five main components: a data collector that collects information generated by any location system available in facilities in order to track movement of staff across the building, a mapping tracker that collects all the timestamps and information generated by the different systems tracking movement associated with an anonymized identifier for a person in order to generate a path for the person, an exposure detector that analyzes interactions between professionals to determine exposures, an infection risk model that estimates the risk of infection resulting from each exposure, and a moves and layout optimizer. In accordance with the operations performed by the moves and layout optimizer, using the information provided by the exposure detector and the infection risk model, the moves and layout optimizer generates safe paths for different professionals and patients within the healthcare facility. This path generation may consider the probability of getting infected provided by the infection risk model, the areas the professional have to traverse, and the hot spots detected in the exposure detection model.

Definitions of Certain Terms

The term "location data object" may refer to an electronically-stored data construct that is configured to describe a measure of location of placement of a corresponding presence-detecting sensor device relative to one or more other location data objects associated with one or more other presence-detecting sensor devices. For example, a particular location data object may describe the measure of location of placement of a Wi-Fi device. As another example, a particular location data object may describe the measure of location of placement of a badge reader device. As yet another example, a particular location data object may describe the measure of location of placement of a Bluetooth sensor device. As a further example, a particular location data object may describe the measure of location of placement of a camera device. Examples of location measures described by location data object include absolute location measures (e.g., absolute location measures described in accordance with the Global Positioning System (GPS)) as well as relative location measures (e.g., relative location measures that describe the location of a particular presence-detecting sensor device with respect to the locations of one or more other presence-detecting sensor devices). The location data object may be a one-dimensional array or a two-dimensional array.

The term "presence-detecting sensor device" may refer to an electronically-stored data construct that is configured to describe an electronic device that is configured to detect the presence of an end-user and/or the presence of an end-user device within a locational proximity of the presence-detecting sensor device. Examples of presence-detecting sensor devices include Wi-Fi devices, badge reader devices, Bluetooth sensor devices, camera devices, voice detection devices, and/or the like. As described above, presence-detecting sensor devices may be configured to generate location data objects. In some embodiments, when combined, location data objects may be used to generate a traversal network.

The term "traversal network" may refer to an electronically-stored data construct that is configured to describe one or more locations described by one or more location data objects as well as detected/assumed/given paths between pairs of the noted locations. The traversal network may, in some embodiments, be a graph data object that describes the locations as tracked location nodes and paths between pairs of locations as traversal edges. Because locations described by a traversal network are determined based at least in part on locational information provided by location data objects, and because location data objects are generated by presence-detecting sensor devices, the tracked location nodes of the traversal network describing the locations are in turn associated with the presence-detecting sensor devices, such that every tracked location node describes a location of a monitored environment, where presence of end-users and/or end-user devices within a positional proximity of the noted monitored environment is being monitored by a respective presence-detecting sensor device. The traversal network may be represented as a two-dimensional array.

The term "traversal agent data object" may refer to an electronically-stored data construct that is configured to describe an agent (e.g., a person such as a patient or a healthcare worker, a bed carrying a person, and/or the like) that intends to travel from a first location within a physical environment of a traversal network to a second location within a physical environment of the traversal network. In some embodiments, the traversal agent data object is associated with a current location that is associated with a source node of the tracked location nodes of the noted traversal network.

The term "candidate traversal path" may refer to an electronically-stored data construct that is configured to describe a sequence of tracked location nodes in a traversal network along with a timestamp for each tracked location node in the sequence. For example, a candidate traversal path may describe a proposed path that a healthcare worker may take to reach a target destination. As another example, a candidate traversal path may describe a proposed route for carrying a patient bed to a target destination such as a surgery room, a medical imaging facility room, and/or the like. As previously noted, each tracked location node described by a candidate traversal path is associated with a timestamp, where the timestamp may be determined based at least in part on a measure of temporality that is common across all candidate traversal paths, such that the timestamps can be used to determine predicted infectious encounters between a candidate traversal path and one or more other infectious traversal paths. A candidate traversal path may thus be associated with one or more node visitation recommendations, where each node visitation recommendation describes a proposed visitation of a tracked location node at a corresponding timestamp as recommended by the candidate traversal path. In some embodiments, to generate a candidate traversal path for a traversal agent data object, a predictive data analysis computing entity identifies a source node within the tracked location nodes of the traversal network that describes a current location of the traversal agent data object, as well as a destination node within the tracked location nodes of the traversal network that describes a destination location of the traversal agent data object. For example, the source node may describe a current location of a patient bed, while the destination node may describe a surgery room to which the patient bed should be transported. In some of the noted embodiments, the predictive data analysis computing entity generates the candidate traversal path as a path that connects the source node and the destination node via one or more traversal edges. The candidate traversal path may be represented as a linked list of node visitation recommendations.

The term "predicted infectious encounter profile" may refer to an electronically-stored data construct that is configured to describe a subset of the node visitation recommendations described by a corresponding candidate traversal path that is predicted to cause likely exposure to an infection. For example, the predicted infectious encounter profile may describe a subset of the node visitation recommendations described by a corresponding candidate traversal path, where each node visitation recommendation in the subset proposes visiting particular tracked location nodes at timestamps that are deemed to be within defined temporal proximity regions of infectious visitation timestamps by traversal agent data objects deemed to be infected. As another example, the predicted infectious encounter profile may describe a subset of the node visitation recommendations described by a corresponding candidate traversal path, where each node visitation recommendation in the subset proposes visiting particular tracked location nodes that are deemed to be at all times infectious or at timestamps deemed to be within a defined temporal proximity region of the timestamp of the node visitation recommendation in the subset. The predicted infectious encounter profile may be represented as an outer linked list of node visitation recommendations.

The term "predicted infectious encounter" may refer to an electronically-stored data construct that is configured to describe a node visitation recommendation that is deemed to cause likely exposure to an infection based at least in part on the tracked location node of the node visitation recommendation and the timestamp of the node visitation recommendation. For example, a predicted infectious encounter may describe a node visitation recommendation that proposes visiting a tracked location node at a first time, where the first time is within a temporal proximity region of a second time associated with visitation of the particular tracked location node by an infectious individual. As another example, a predicted infectious encounter may describe a node visitation recommendation that proposes visiting a tracked location node that is deemed to be infectious at all times, such as infection hub including a cafeteria, an intensive care unit (ICU), and/or the like. As yet another example, a predicted infectious encounter may describe a node visitation recommendation that proposes visiting a tracked location node that is deemed to be infectious at particular times, where the particular times are within a temporal proximity region of the timestamp of the node visitation recommendation. The predicted infectious encounter may be represented as a one-dimensional vector representing a corresponding node visitation recommendation.

The term "path risk" may refer to an electronically-stored data construct that is configured to describe an estimated measure of infectious/viral exposure risk for a candidate traversal path. In some embodiments, a predictive data analysis computing entity generates the path risk score based at least in part on each predicted total VPI measure associated with a predicted infectious encounter for the candidate traversal path. In some embodiments, to generate the predicted risk score for the candidate traversal path, the predictive data analysis computing entity generates a predicted VPI measure for each predicted infectious encounter that is deemed to be associated with the candidate traversal path based at least in part on the cross-node infectious encounter profile for the candidate traversal path.

The term "predicted VPI measure" may refer to an electronically-stored data construct that is configured to describe an estimated/predicted quantity of infectious/viral particles inhaled by a person described by a traversal agent data object when the person faces the circumstances described by a corresponding predicted infectious encounter. In some embodiments, a predicted VPI measure is determined based at least in part on a predicted respiration rate measure for the traversal agent data object, a predicted tidal volume measure for the traversal agent data object, and a predicted cumulative VPD measure for the traversal agent data object across a predicted length of the corresponding predicted infectious encounter. In some embodiments, the predicted VPI measure is determined in accordance with the equation $VPI_{Total} = RR \times TV \times \Sigma_{t=1}^{T} VPD_t$, where $VPI_{Total}$ is the predicted total VPI measure, RR is the predicted respiration rate measure, TV is the predicted tidal volume measure, and $\Sigma_{t=1}^{T} VPD_t$ is the predicted total VPD measure.

The term "predicted respiration rate measure" may refer to an electronically-stored data construct that is configured to describe the estimated/predicted/expected respiration rate of a person described by a traversal agent data object when the person faces the circumstances described by a corresponding predicted infectious encounter. In some embodiments, the predicted respiration rate is determined based at least in part on a normal respiration rate for an adult at rest, which is between 12 to 20 breaths per minute.

The term "predicted tidal volume measure" may refer to an electronically-stored data construct that is configured to describe the estimated/estimated/expected tidal volume of a person described by a traversal agent data object when the person faces the circumstances described by a corresponding predicted infectious encounter. In some embodiments, the predicted tidal volume measure is determined based at least in part on the tidal volume of a young human adult, which is 500 milliliters per inspiration or 0.0005 cubic meter.

The term "predicted total VPD measure" may refer to an electronically-stored data construct that is configured to describe the estimated/predicted density of viral/infectious particle density within a physical environment of a corresponding predicted infectious encounter. In some embodiments, the predicted total VPD measure is determined based at least in part on per-time-unit predicted VPD measures across time units of a time length of the corresponding predicted infectious encounter. In some embodiments, the predicted total VPD measure is determined based at least in part on the equation $VPD_{Total} = \Sigma_{t=1}^{T} VPD_t$, where $VPD_{Total}$ is the predicted total VPD measure and $VPD_t$ is a per-time-unit predicted VPD measure in a time unit of the time length of the corresponding predicted infectious encounter.

The term "per-time-unit predicted VPD measure" may refer to an electronically-stored data construct that is configured to describe an estimated/predicted density of viral/infectious particle density within a physical environment of a corresponding predicted infectious encounter during a time unit (e.g., a second) of a time length of the corresponding infectious encounter. In some embodiments, a per-time-unit predicted VPD measure for a time unit is determined based at least in part on a total predicted viral particle release (VPR) measure by an infectious individual up to the time unit and a room volume measure for an encounter location associated with the predicted infectious encounter.

Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware framework and/or operating system platform. A software component comprising assembly language instructions may require conversion into executable machine code by an assembler prior to execution by the hardware framework and/or platform. Another example programming language may be a higher-level programming language that may be portable across multiple frameworks. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatuses, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

Exemplary System Framework

FIG. 1 is a schematic diagram of an example system architecture 100 for performing predictive data analysis steps/operations and generating corresponding user interface data (e.g., for providing and/or updating a user interface). The system architecture 100 includes a predictive data analysis system 101 comprising a predictive data analysis computing entity 106 configured to generate predictive outputs that lead to performing one or more prediction-based actions. The predictive data analysis system 101 may communicate with one or more external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like). An example of a prediction that may be generated by using the system architecture 100 includes a prediction related to safe traversal paths within traversal networks. An example of a prediction-based action that may be performed using the system architecture 100 includes controlling access to various locations within a building based on predictions related to safe traversal paths within traversal networks.

The system architecture 100 includes a storage subsystem 108 configured to store at least a portion of the data utilized by the predictive data analysis system 101. The predictive data analysis computing entity 106 may be in communication with one or more external computing entities 102. The predictive data analysis computing entity 106 may be configured to receive requests and/or data from external computing entities 102, process the requests and/or data to generate predictive outputs (e.g., predictive data analysis data objects), and provide the predictive outputs to the external computing entities 102. The external computing entity 102 (e.g., management computing entity) may periodically update/provide raw input data (e.g., data objects describing primary events and/or secondary events) to the predictive data analysis system 101. The external computing entities 102 may further generate user interface data (e.g., one or more data objects) corresponding to the predictive outputs and may provide (e.g., transmit, send and/or the like) the user interface data corresponding with the predictive outputs for presentation to user computing entities operated by end-users.

The storage subsystem 108 may be configured to store at least a portion of the data utilized by the predictive data analysis computing entity 106 to perform predictive data analysis steps/operations and tasks. The storage subsystem 108 may be configured to store at least a portion of operational data and/or operational configuration data including operational instructions and parameters utilized by the predictive data analysis computing entity 106 to perform predictive data analysis steps/operations in response to requests. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

Figure 2:
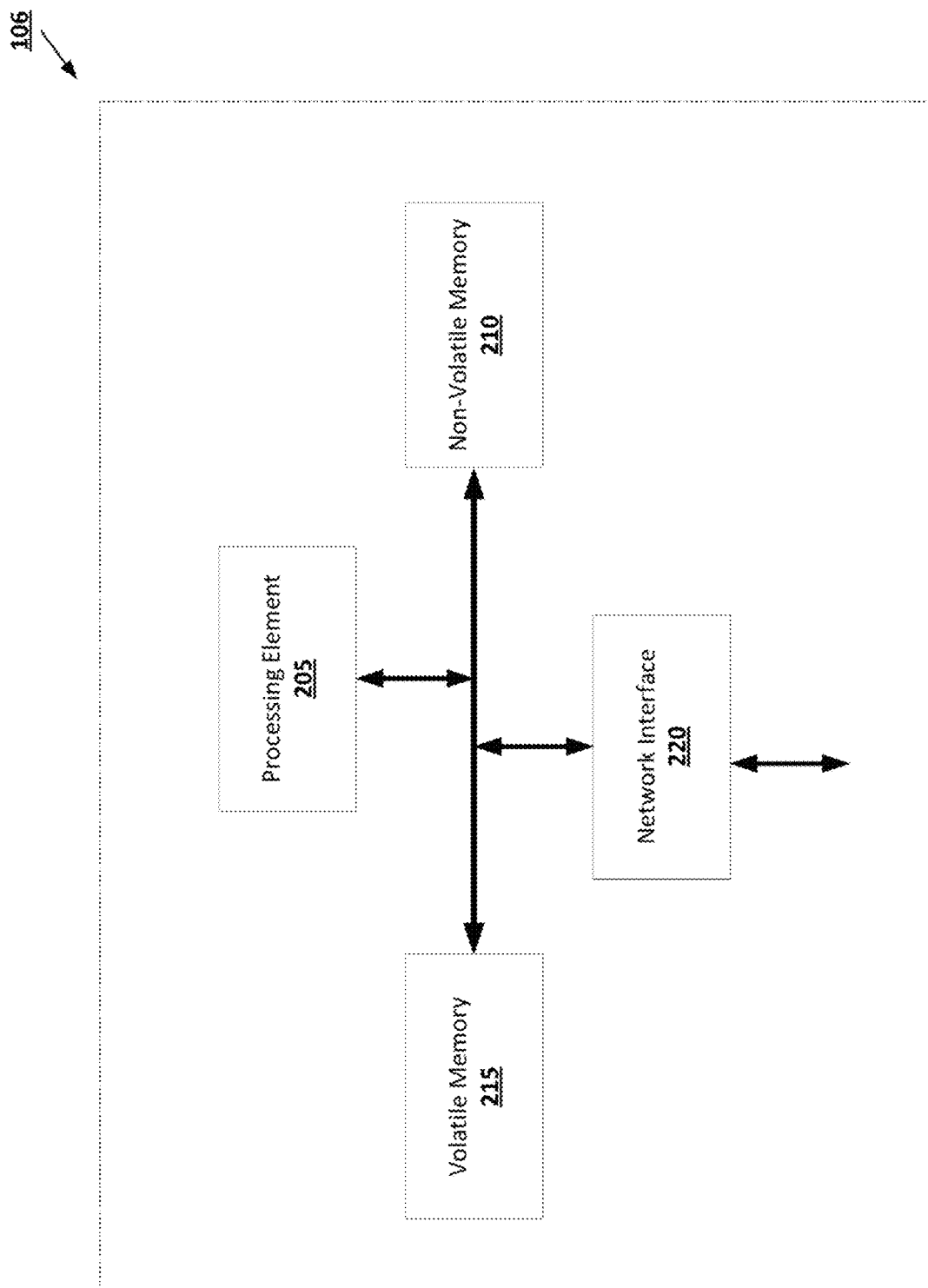

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. Such functions, steps/operations, and/or processes may include, for example, transmitting, receiving, operating on, processing, displaying, storing, determining, creating/generating, monitoring, evaluating, comparing, and/or similar terms used herein interchangeably. In one embodiment, these functions, steps/operations, and/or processes can be performed on data, content, information, and/or similar terms used herein interchangeably.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with a processing element 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include at least one non-volatile memory 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include at least one volatile memory 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

Figure 3:
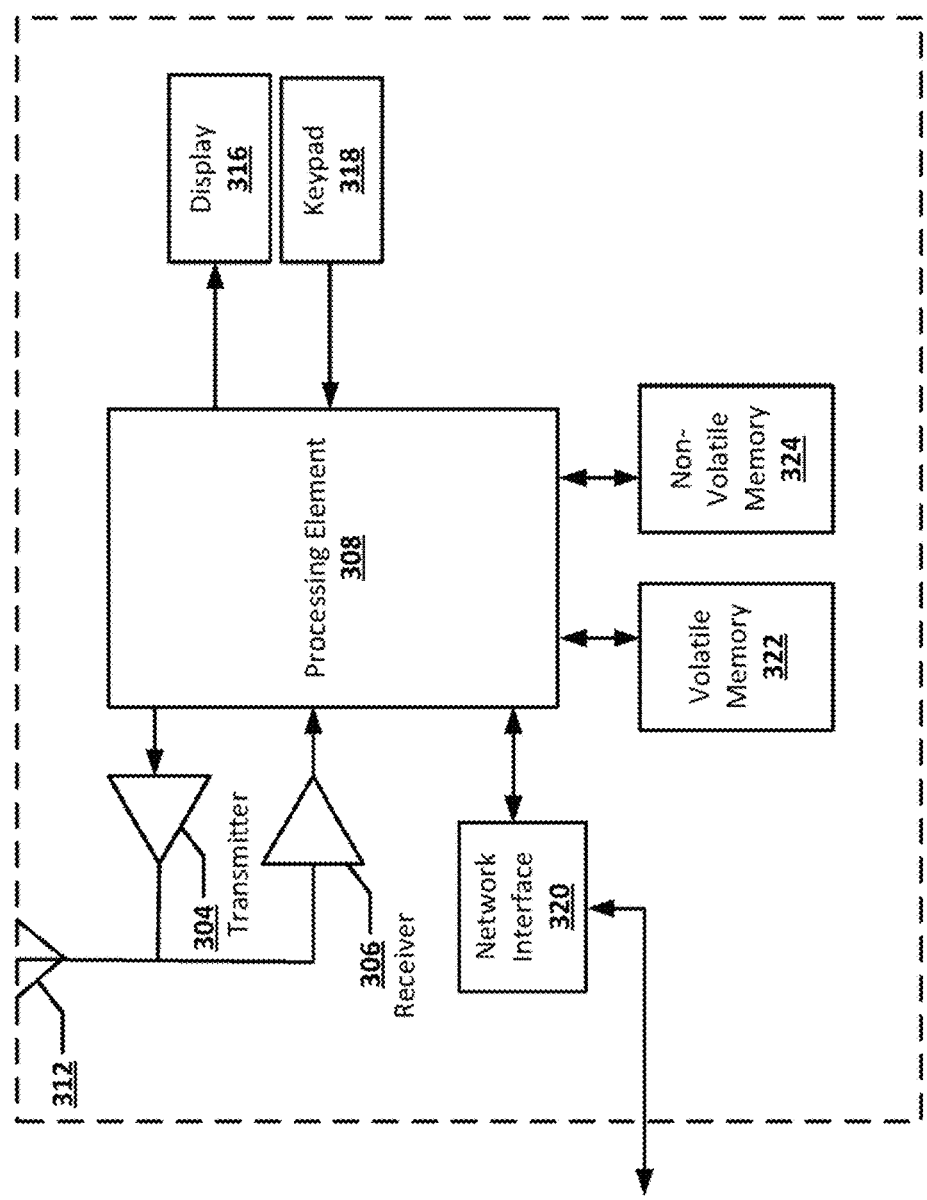

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS))). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these frameworks and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

Exemplary System Operations

Various embodiments of the present invention provide techniques for efficiently and effectively traversing an infection network by performing graph-based inferences about agent co-visitation as well as agent visitation of high-risk areas before performing computationally resource-intensive infection risk modeling operations. The graph-based techniques introduced herein enable substantially shrinking the number of risk modeling iterations that need to be performed as part of generating traversal paths across traversal networks, as temporal path occurrence information about traversal of various agents are used to focus the focus of the risk modeling analysis on identified path co-occurrences, rather than on all possible pair of traversal paths. Because of this, various embodiments of the present invention are able to perform network-wide infection risk modeling in a computationally efficient manner and by using fewer processing cycles. In this way, various embodiments of the present invention improve computational efficiency of performing network-wide risk modeling and disclose innovative and technologically advantageous solutions for performing faster network-wide risk modeling, a feature that in turn enables performing network-wide risk modeling operations in a real-time or near-real-time manner.

Determining Optimal Traversal Paths

Figure 4:
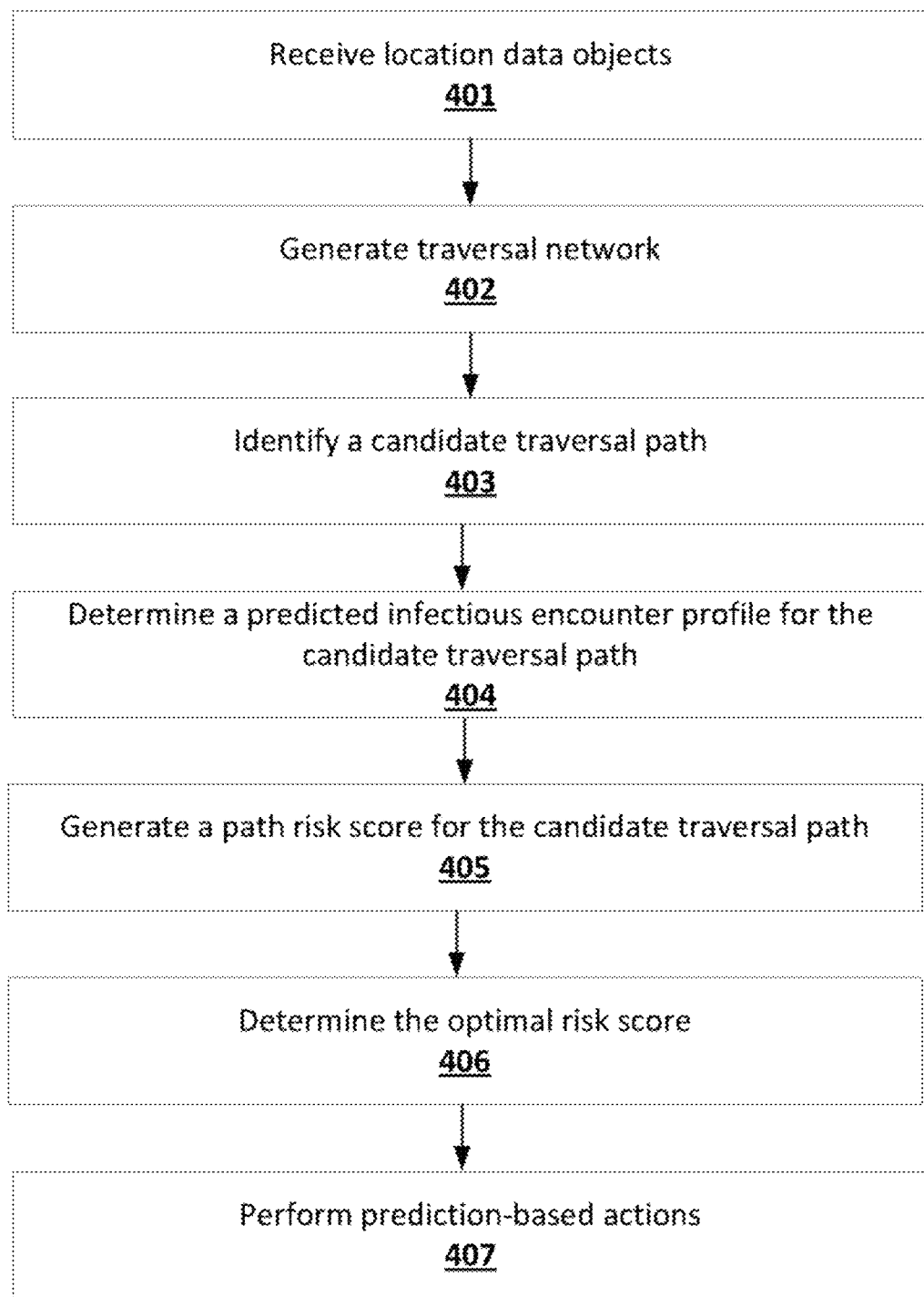

FIG. 4 is a flowchart diagram of an example process 400 for determining an optimal traversal path within a traversal network for a traversal agent data object. Via the various steps/operations of the process 400, the predictive data analysis computing entity 106 can utilize graph-based traversal modeling to efficiently detect predicted infectious encounters and use the detected predicted infectious encounters to perform infection risk modeling based at least in part on predicted total VPI measures for predicted infectious encounter measures.

The process 400 begins at step/operation 401 when the predictive data analysis computing entity 106 receives one or more location data objects from one or more presence-detecting sensor devices. For example, the predictive data analysis computing entity 106 may receive location data objects from at least one of one or more Wi-Fi devices, one or more badge reader devices, one or more Bluetooth sensor devices, one or more camera devices, one or more voice detection devices, and/or the like.

In general, a location data object may describe a measure of location of placement of a corresponding presence-detecting sensor device relative to one or more other location data objects associated with one or more other presence-detecting sensor devices. For example, a particular location data object may describe the measure of location of placement of a Wi-Fi device. As another example, a particular location data object may describe the measure of location of placement of a badge reader device. As yet another example, a particular location data object may describe the measure of location of placement of a Bluetooth sensor device. As a further example, a particular location data object may describe the measure of location of placement of a camera device. Examples of location measures described by location data object include absolute location measures (e.g., absolute location measures described in accordance with the Global Positioning System (GPS)) as well as relative location measures (e.g., relative location measures that describe the location of a particular presence-detecting sensor device with respect to the locations of one or more other presence-detecting sensor devices).

A presence-detecting sensor device may describe an electronic device that is configured to detect the presence of an end-user and/or the presence of an end-user device within a locational proximity of the presence-detecting sensor device. Examples of presence-detecting sensor devices include Wi-Fi devices, badge reader devices, Bluetooth sensor devices, camera devices, voice detection devices, and/or the like. As described above, presence-detecting sensor devices may be configured to generate location data objects. In some embodiments, when combined, location data objects may be used to generate a traversal network.

FIG. 5 provides an operational example of an exemplary data schema 500 for a location data object. As depicted in FIG. 5, the data schema 500 includes: (i) a Device ID field that is configured to describe the presence-detecting sensor device that is associated with the location data object, (ii) a Device Type field that is configured to describe a type of the presence-detecting sensor device that is associated with the location data object, (iii) a Device Location field that is configured to describe at least one of the location of the presence-detecting sensor device that is associated with the location data object or a location measure generated by the presence-detecting sensor device that is associated with the location data object, (iv) a Creation Timestamp field that is configured to describe a time when the presence-detecting sensor device that is associated with the location data object generated the location data object, and (v) and a Validity Duration that is configured to describe a time period within which the location measure described by the location data object can be deemed to remain valid.

Returning to FIG. 4, at step/operation 402, the predictive data analysis computing entity 106 generates a traversal network based at least in part on the location data objects. In some embodiments, the predictive data analysis computing entity 106 combines the locational information inferred based at least in part on the location data objects to generate the traversal network.

A traversal network may describe one or more locations described by one or more location data objects as well as detected/assumed/given paths between pairs of the noted locations. The traversal network may, in some embodiments, be a graph data object that describes the locations as tracked location nodes and paths between pairs of locations as traversal edges. Because locations described by a traversal network are determined based at least in part on locational information provided by location data objects, and because location data objects are generated by presence-detecting sensor devices, the tracked location nodes of the traversal network describing the locations are in turn associated with the presence-detecting sensor devices, such that every tracked location node describes a location of a monitored environment, where presence of end-users and/or end-user devices within a positional proximity of the noted monitored environment is being monitored by a respective presence-detecting sensor device.

Figure 6:
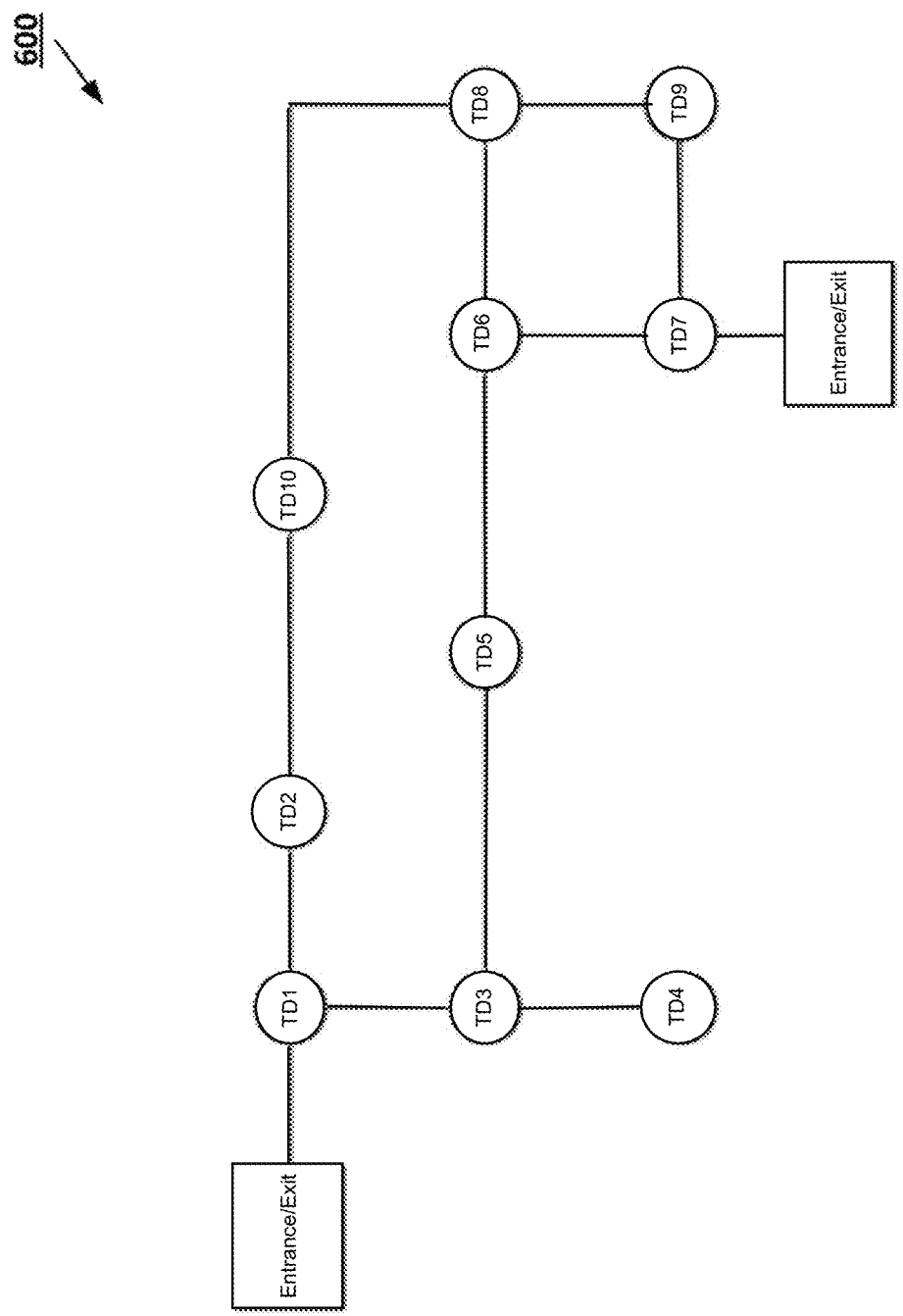

An operational example of a traversal network 600 is depicted in FIG. 6. As depicted in FIG. 6, the traversal network 600 is associated with ten tracked location nodes TD1-TD10. As further depicted in FIG. 6, the traversal network 600 is associated with the following traversal edges: a traversal edge between the tracked location node TD1 and the tracked location node TD2, a traversal edge between the tracked location node TD1 and the tracked location node TD3, a traversal edge between the tracked location node TD2 and the tracked location node TD10, a traversal edge between the tracked location node TD8 and the tracked location node TD10, a traversal edge between the tracked location node TD3 and the tracked location node TD4, a traversal edge between the tracked location node TD3 and the tracked location node TD5, a traversal edge between the tracked location node TD5 and the tracked location node TD6, a traversal edge between the tracked location node TD6 and the tracked location node TD8, a traversal edge between the tracked location node TD8 and the tracked location node TD9, a traversal edge between the tracked location node TD6 and the tracked location node TD7, and a traversal edge between the tracked location node TD7 and the tracked location node TD9.

Returning to FIG. 4, at step/operation 403, the predictive data analysis computing entity 106 identifies a candidate traversal path for a traversal agent data object. For example, the predictive data analysis computing entity 106 may generate a candidate traversal path for a traversal agent data object that is associated with a healthcare worker in a healthcare facility. As another example, the predictive data analysis computing entity 106 may generate a candidate traversal path for a traversal agent that object that is associated with a patient in a healthcare facility.

In general, a traversal agent data object describes an agent (e.g., a person such as a patient or a healthcare worker, a bed carrying a person, and/or the like) that intends to travel from a first location within a physical environment of a traversal network to a second location within a physical environment of the traversal network. In some embodiments, the traversal agent data object is associated with a current location that is associated with a source node of the tracked location nodes of the noted traversal network.

A candidate traversal path may describe a sequence of tracked location nodes in a traversal network along with a timestamp for each tracked location node in the sequence. For example, a candidate traversal path may describe a proposed path that a healthcare worker may take to reach a target destination. As another example, a candidate traversal path may describe a proposed route for carrying a patient bed to a target destination such as a surgery room, a medical imaging facility room, and/or the like. As previously noted, each tracked location node described by a candidate traversal path is associated with a timestamp, where the timestamp may be determined based at least in part on a measure of temporality that is common across all candidate traversal paths, such that the timestamps can be used to determine predicted infectious encounters between a candidate traversal path and one or more other infectious traversal paths. A candidate traversal path may thus be associated with one or more node visitation recommendations, where each node visitation recommendation describes a proposed visitation of a tracked location node at a corresponding timestamp as recommended by the candidate traversal path.

In some embodiments, to generate a candidate traversal path for a traversal agent data object, the predictive data analysis computing entity 106 identifies a source node within the tracked location nodes of the traversal network that describes a current location of the traversal agent data object, as well as a destination node within the tracked location nodes of the traversal network that describes a destination location of the traversal agent data object. For example, the source node may describe a current location of a patient bed, while the destination node may describe a surgery room to which the patient bed should be transported. In some of the noted embodiments, the predictive data analysis computing entity 106 generates the candidate traversal path as a path that connects the source node and the destination node via one or more traversal edges.

Figure 7A:
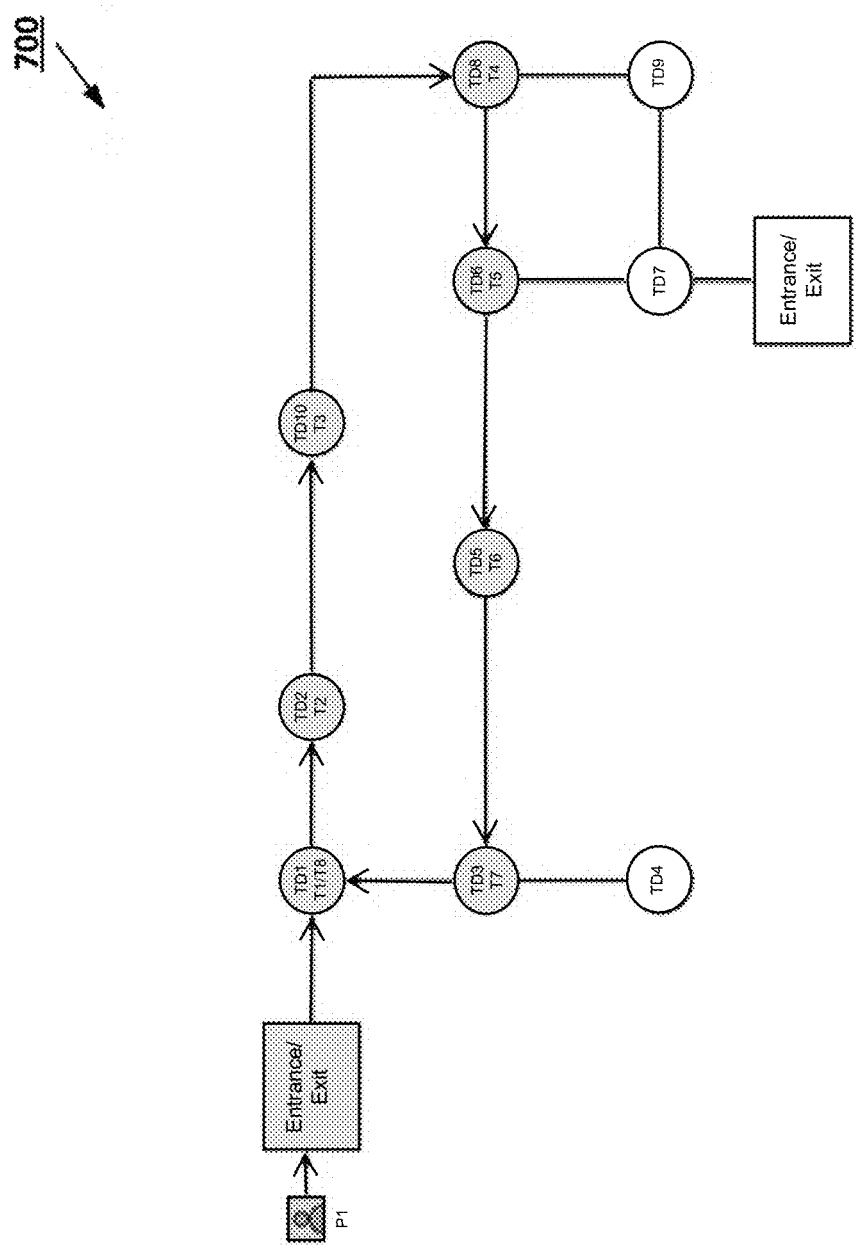

An operational example of a candidate traversal path 700 is depicted in FIG. 7A. As depicted in FIG. 7A, the candidate traversal path 700 describes a path for the traversal agent data object P1 that includes: crossing the tracked location node TD1 at time T1, crossing the tracked location node TD2 at time T2, crossing the tracked location node TD10 at time T3, crossing the tracked location node TD8 at time T4, crossing the tracked location node TD6 at time T5, crossing the tracked location node TD5 at time T6, crossing the tracked location node TD3 at time T7, and crossing the tracked location node TD1 at time T8.

Figure 7B:
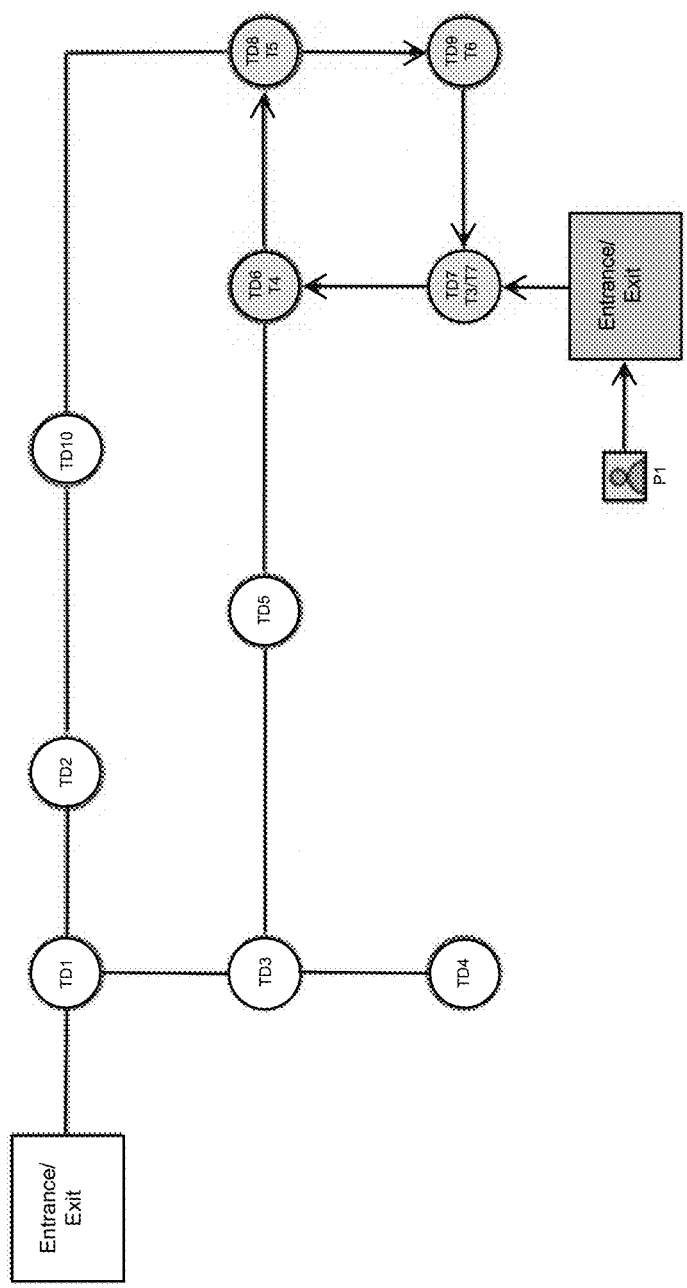

Another operational example of a candidate traversal path 750 is depicted in FIG. 7B. As depicted in FIG. 7B, the candidate traversal path 750 describes a path for the traversal agent data object P1 that includes: crossing the tracked location node TD7 at time T3, crossing the tracked location node TD6 at time T4, crossing the tracked location node TD8 at time T5, crossing the tracked location node TD9 at time T6, and crossing the tracked location node TD7 at time T7.

Figure 8:

FIG. 8 provides an operational example of a node visitation recommendation data object 800 that describes the node visitation recommendations associated with both of the candidate traversal path 700 of FIG. 7A and the candidate traversal path 750 of FIG. 7B. As depicted in FIG. 8, the node visitation recommendation data object 800 describes the following node visitation recommendations for the candidate traversal path 700: a node visitation recommendation that describes visiting location TD1 at timestamp T1 by the traversal agent data object P1, a node visitation recommendation that describes visiting location TD2 at timestamp T2 by the traversal agent data object P1, a node visitation recommendation that describes visiting location TD10 at timestamp T1 by the traversal agent data object P3, a node visitation recommendation that describes visiting location TD8 at timestamp T4 by the traversal agent data object P1, a node visitation recommendation that describes visiting location TD6 at timestamp T5 by the traversal agent data object P1, a node visitation recommendation that describes visiting location TD5 at timestamp T6 by the traversal agent data object P1, a node visitation recommendation that describes visiting location TD3 at timestamp T7 by the traversal agent data object P1, and a node visitation recommendation that describes visiting location TD1 at timestamp T8 by the traversal agent data object P1.

As further depicted in FIG. 8, the node visitation recommendation data object 800 describes the following node visitation recommendations for the candidate traversal path 750: a node visitation recommendation that describes visiting location TD7 at timestamp T3 by the traversal agent data object P2, a node visitation recommendation that describes visiting location TD6 at timestamp T4 by the traversal agent data object P2, a node visitation recommendation that describes visiting location TD8 at timestamp T5 by the traversal agent data object P2, a node visitation recommendation that describes visiting location TD9 at timestamp T6 by the traversal agent data object P2, and a node visitation recommendation that describes visiting location TD7 at timestamp T7 by the traversal agent data object P2.

Returning to FIG. 4, at step/operation 404, the predictive data analysis computing entity 106 determines a predicted infectious encounter profile for the candidate traversal path, where the predicted infectious encounter profile describes one or more predicted infectious encounters for the traversal agent data object that is associated with the candidate traversal path. In some embodiments, the predictive data analysis computing entity 106 generates the predicted infectious encounter profile based at least in part on at least one of one or more infectious traversal paths or one or more infectious region designations.

A predicted infectious encounter profile for a traversal path describes a subset of the node visitation recommendations described by a corresponding candidate traversal path that is predicted to cause likely exposure to an infection. For example, the predicted infectious encounter profile may describe a subset of the node visitation recommendations described by a corresponding candidate traversal path, where each node visitation recommendation in the subset proposes visiting particular tracked location nodes at timestamps that are deemed to be within defined temporal proximity regions of infectious visitation timestamps by traversal agent data objects deemed to be infected. As another example, the predicted infectious encounter profile may describe a subset of the node visitation recommendations described by a corresponding candidate traversal path, where each node visitation recommendation in the subset proposes visiting particular tracked location nodes that are deemed to be at all times infectious or at timestamps deemed to be within a defined temporal proximity region of the timestamp of the node visitation recommendation in the subset.

A predicted infectious encounter may describe a node visitation recommendation that is deemed to cause likely exposure to an infection based at least in part on the tracked location node of the node visitation recommendation and the timestamp of the node visitation recommendation. For example, a predicted infectious encounter may describe a node visitation recommendation that proposes visiting a tracked location node at a first time, where the first time is within a temporal proximity region of a second time associated with visitation of the particular tracked location node by an infectious individual. As another example, a predicted infectious encounter may describe a node visitation recommendation that proposes visiting a tracked location node that is deemed to be infectious at all times, such as infection hub including a cafeteria, an intensive care unit (ICU), and/or the like. As yet another example, a predicted infectious encounter may describe a node visitation recommendation that proposes visiting a tracked location node that is deemed to be infectious at particular times, where the particular times are within a temporal proximity region of the timestamp of the node visitation recommendation.

Figure 9:
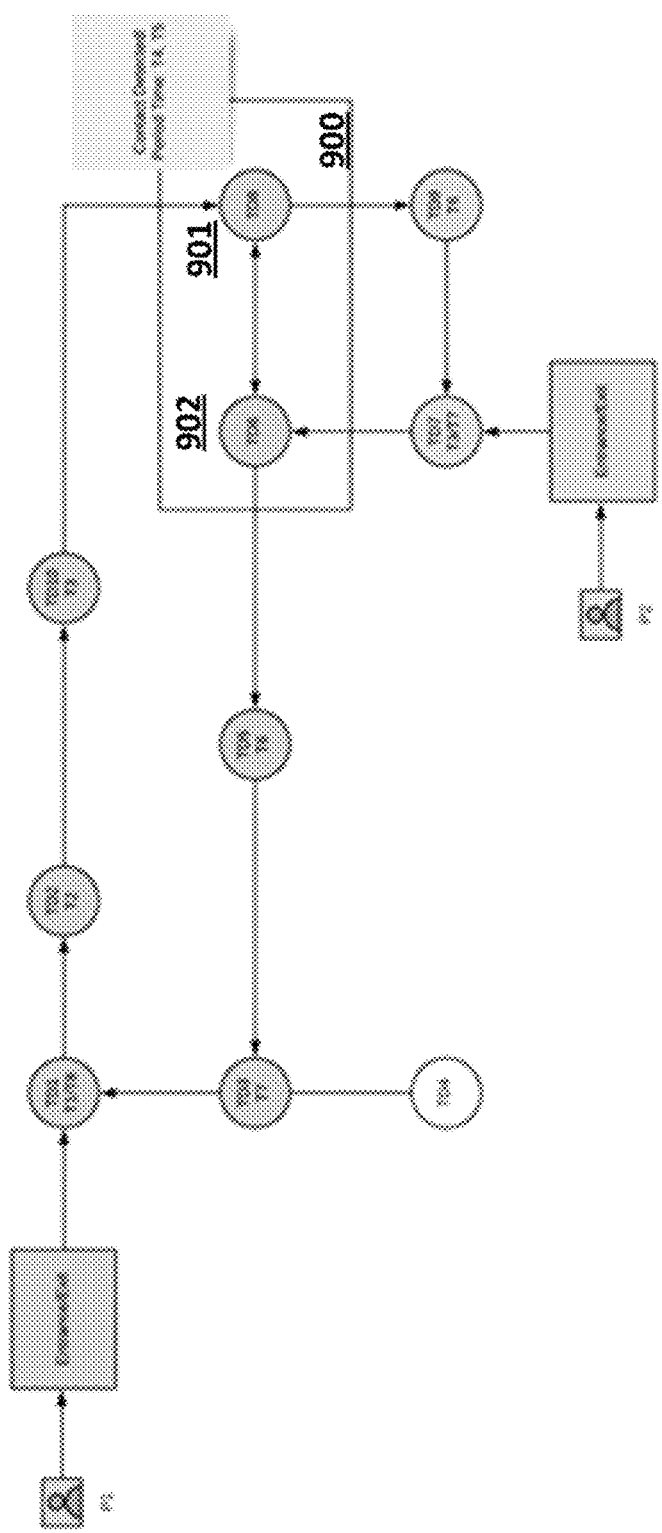

An operational example of generating a predicted infectious encounter profile 900 for the candidate traversal path 700 that is associated with the traversal agent data object P1 is depicted in FIG. 9. As depicted in FIG. 9, the predicted infectious encounter profile 900 describes a predicted infectious encounter 901 associated with the node visitation recommendation corresponding to traversal agent data object P1's proposed visitation of the tracked location node TD8 at timestamp T4, as well as a predicted infectious encounter 902 associated with the node visitation recommendation corresponding to traversal agent data object P1's proposed visitation of the tracked location node TD6 at timestamp T5. In some embodiments, the predicted infectious encounter 901 may be generated because the traversal agent data object P2 (which is deemed to be an infectious traversal agent data object) is expected to visit the tracked location node TD8 at timestamp T5, which is within a temporal proximity region of the timestamp T4. Moreover, the predicted infectious encounter 902 may be generated because the traversal agent data object P2 (which is deemed to be an infectious traversal agent data object) is expected to visit the tracked location node TD6 at timestamp T4, which is within a temporal proximity region of the timestamp T5.

Returning to FIG. 4, at step/operation 405, the predictive data analysis computing entity 106 generates a path risk score for the candidate traversal path. In some embodiments, the predictive data analysis computing entity 106 generates the path risk score based at least in part on each predicted total VPI measure associated with a predicted infectious encounter for the candidate traversal path.

In some embodiments, to generate the predicted risk score for the candidate traversal path, the predictive data analysis computing entity 106 generates a predicted VPI measure for each predicted infectious encounter that is deemed to be associated with the candidate traversal path based at least in part on the cross-node infectious encounter profile for the candidate traversal path. A predicted VPI measure may describe an estimated/predicted quantity of infectious/viral particles inhaled by a person described by a traversal agent data object when the person faces the circumstances described by a corresponding predicted infectious encounter. In some embodiments, a predicted VPI measure is determined based at least in part on a predicted respiration rate measure for the traversal agent data object, a predicted tidal volume measure for the traversal agent data object, and a predicted cumulative VPD measure for the traversal agent data object across a predicted length of the corresponding predicted infectious encounter. In some embodiments, the predicted VPI measure is determined in accordance with the equation $\text{VPI}_{Total} = \text{RR} \times \text{TV} \times \Sigma_{t=1}^{T} \text{VPD}_t$, where $\text{VPI}_{Total}$ is the predicted total VPI measure, RR is the predicted respiration rate measure, TV is the predicted tidal volume measure, and $\Sigma_{t=1}^{T} \text{VPD}_t$ is the predicted total VPD measure.

In some embodiments, a predicted respiration rate measure describes the estimated/predicted/expected respiration rate of a person described by a traversal agent data object when the person faces the circumstances described by a corresponding predicted infectious encounter. In some embodiments, the predicted respiration rate is determined based at least in part on a normal respiration rate for an adult at rest, which is between 12 to 20 breaths per minute.

In some embodiments, a predicted tidal volume measure describes the estimated/estimated/expected tidal volume of a person described by a traversal agent data object when the person faces the circumstances described by a corresponding predicted infectious encounter. In some embodiments, the predicted tidal volume measure is determined based at least in part on the tidal volume of a young human adult, which is 500 milliliters per inspiration or 0.0005 cubic meter.

In some embodiments, the predicted total VPD measure describes the estimated/predicted density of viral/infectious particle density within a physical environment of a corresponding predicted infectious encounter. In some embodiments, the predicted total VPD measure is determined based at least in part on per-time-unit predicted VPD measures across time units of a time length of the corresponding predicted infectious encounter. In some embodiments, the predicted total VPD measure is determined based at least in part on the equation $\text{VPD}_{Total} \Sigma_{t=1}^{T} \text{VPD}_t$, where $\text{VPD}_t$ is a per-time-unit predicted VPD measure in a time unit of the time length of the corresponding predicted infectious encounter.

In some embodiments, a per-time-unit predicted VPD measure describes the estimated/predicted density of viral/infectious particle density within a physical environment of a corresponding predicted infectious encounter during a time unit (e.g., a second) of a time length of the corresponding infectious encounter. In some embodiments, a per-time-unit predicted VPD measure for a time unit is determined based at least in part on a total predicted viral particle release (VPR) measure by an infectious individual up to the time unit and a room volume measure for an encounter location associated with the predicted infectious encounter.

At step/operation 406, the predictive data analysis computing entity 106 determines an optimal traversal path based at least in part on the path risk score. In some embodiments, the predictive data analysis computing entity 106 determines the optimal traversal path based at least in part on each risk path for a candidate traversal path of multiple candidate traversal paths. In some embodiments, the predictive data analysis computing entity 106 selects a path having a lowest path risk score among a group of candidate traversal paths between the source node and the destination node as the optimal traversal path.

Figure 11:
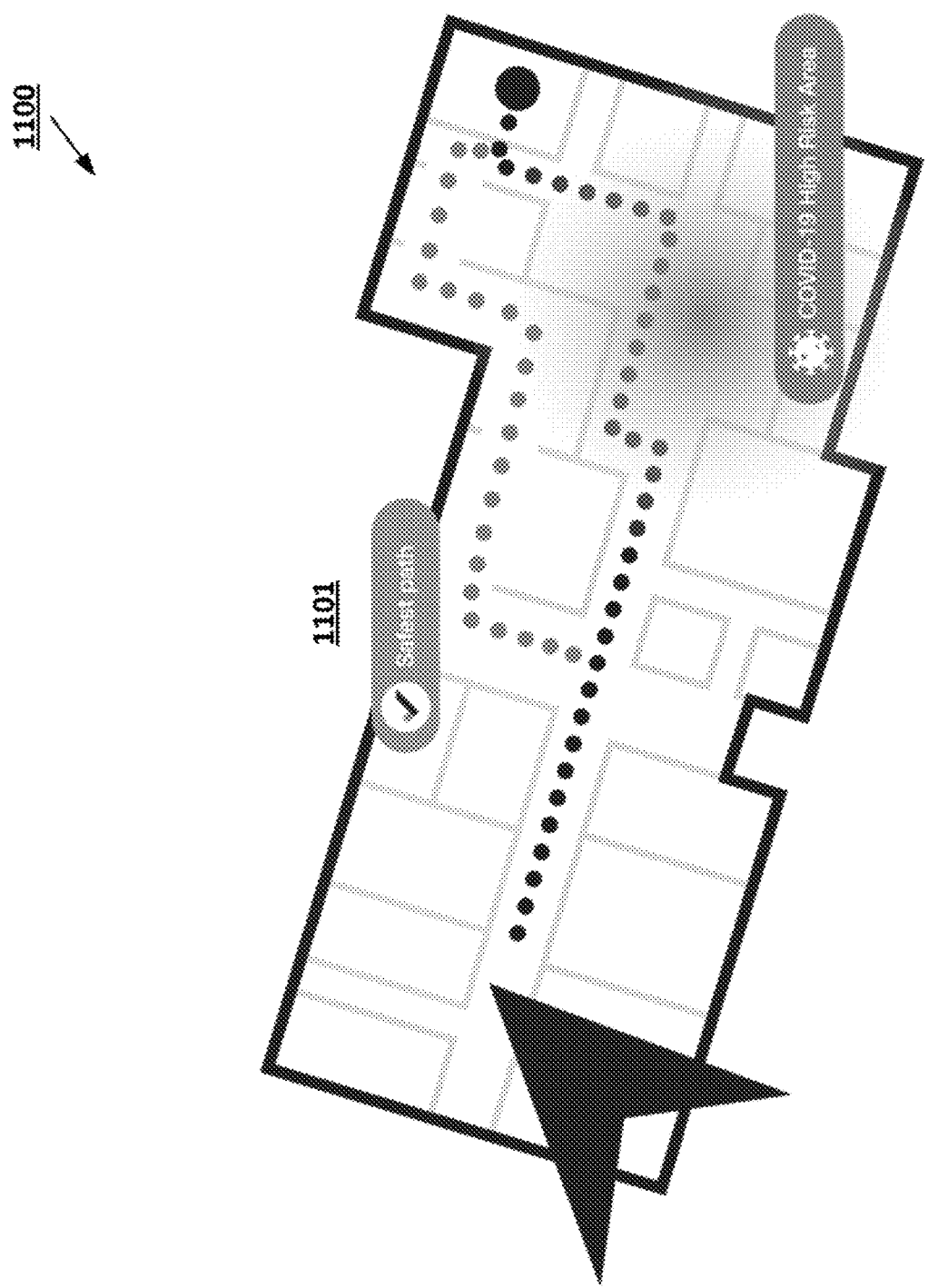
Figure 9:
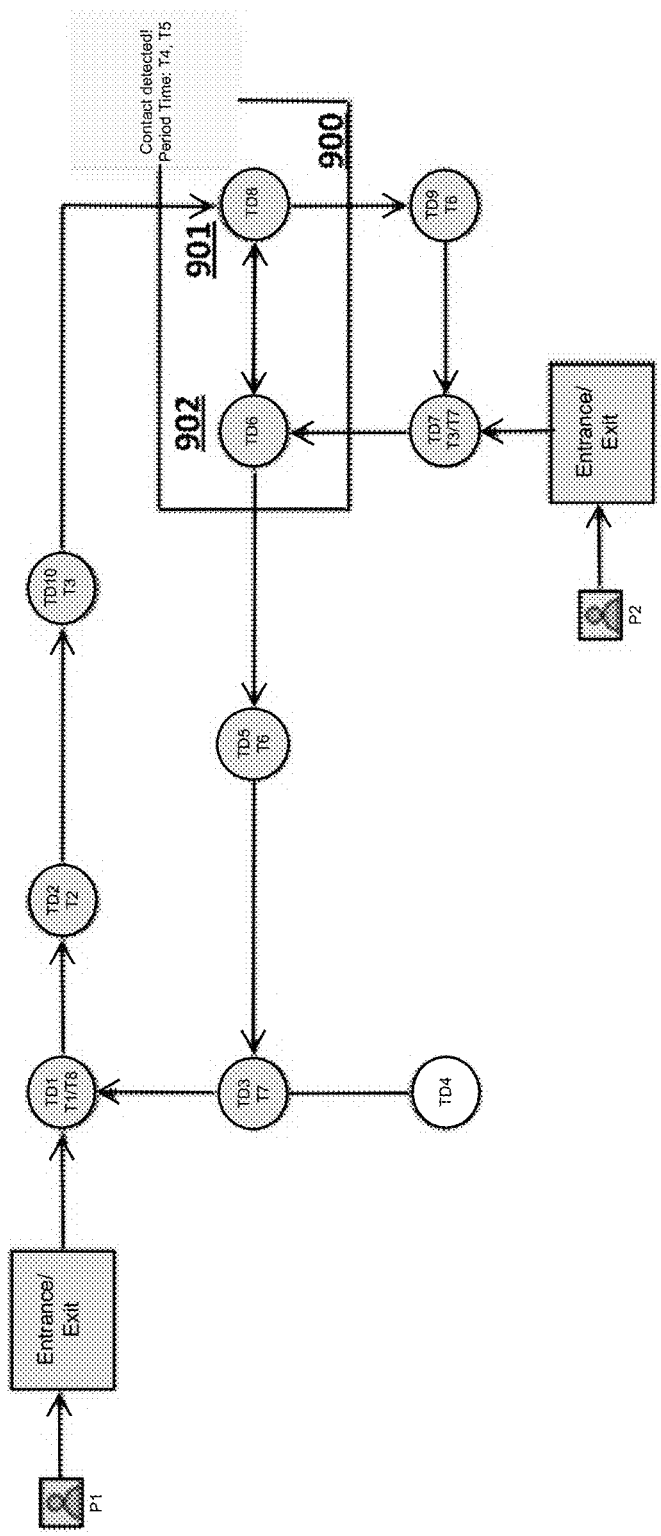
Figure 9:
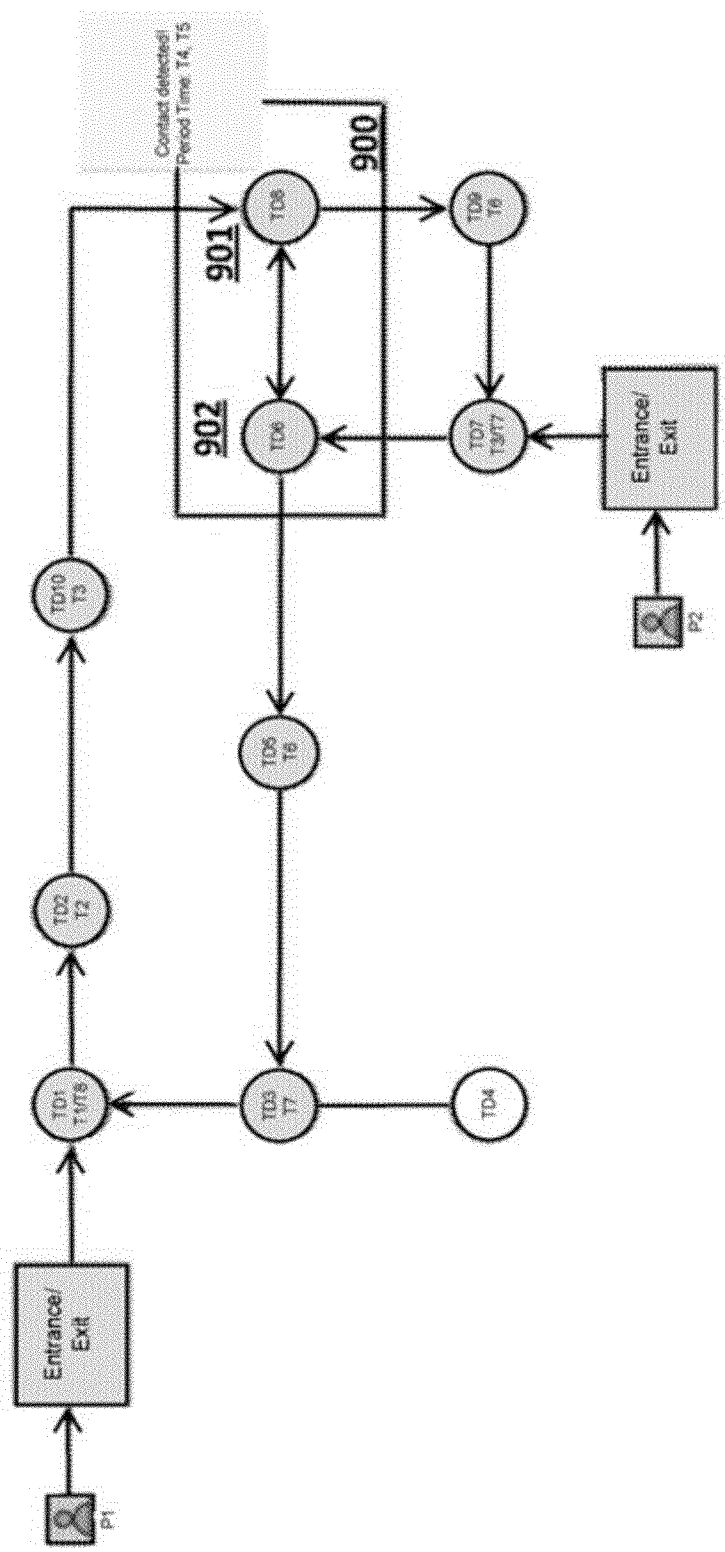

At step/operation 407, the predictive data analysis computing entity 106 performs one or more prediction-based actions based at least in part on the optimal traversal path. In some embodiments, the predictive data analysis computing entity 106 causes an external computing entity 102 to display a prediction output user interface that displays the safest path within a graphical representation of the traversal network. An operational example of such a prediction output user interface 1100 is depicted in FIG. 11. As depicted in FIG. 11, the prediction output user interface 1100 depicts the optimal path 1101.

In some embodiments, to perform the prediction-based actions, the predictive data analysis computing entity 106 sets access parameters for one or more areas (e.g., rooms, hallways, and/or the like) within a building associated with the traversal network in accordance with the optimal traversal path. In some embodiments, the predictive data analysis computing entity 106 sets the access parameters by performing at least one of the following: (i) communicating with one or more networked locks associated with the building, and (ii) communicating with a networked device that controls the configuration of one or more locks associated with the building.

Determining Optimal Traversal Path Lists

Figure 12:
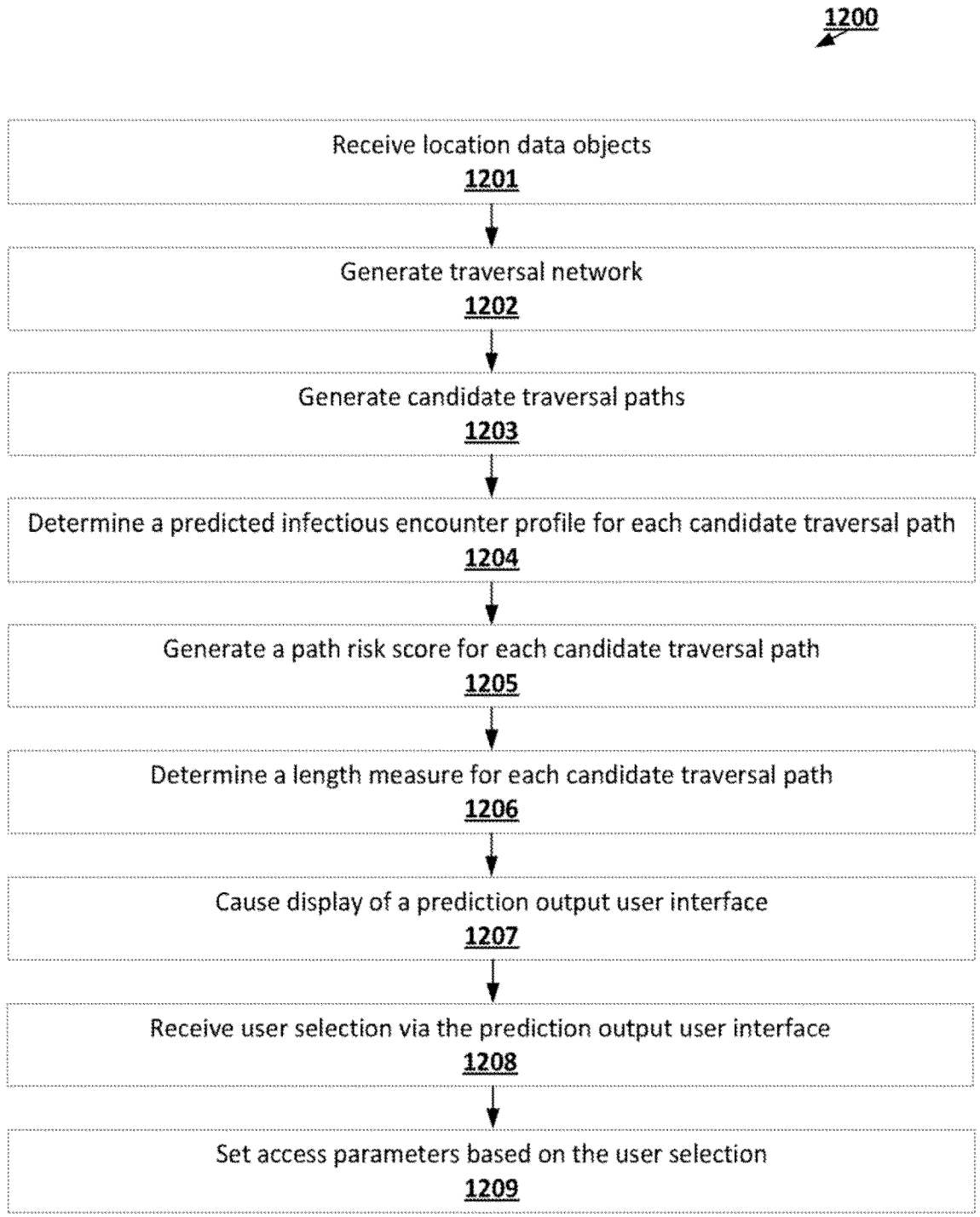

FIG. 12 is a flowchart diagram of an example process 1200 for generating an optimally ranked list of candidate traversal paths. Via the various steps/operations of the process 400, the predictive data analysis computing entity 106 can utilize graph-based traversal modeling to efficiently detect predicted infectious encounters, use the detected predicted infectious encounters to perform infection risk modeling based at least in part on predicted total VPI measures for predicted infectious encounter measures, and use the output of the infection risk modeling to generate ranked lists of optimal traversal paths.

The process 1200 begins at step/operation 1201 when the predictive data analysis computing entity 106 receives one or more location data objects from one or more presence-detecting sensor devices. For example, the predictive data analysis computing entity 106 may receive location data objects from at least one of one or more Wi-Fi devices, one or more badge reader devices, one or more Bluetooth sensor devices, one or more camera devices, one or more voice detection devices, and/or the like.

As described above, a location data object may describe a measure of location of placement of a corresponding presence-detecting sensor device relative to one or more other location data objects associated with one or more other presence-detecting sensor devices. For example, a particular location data object may describe the measure of location of placement of a Wi-Fi device. As another example, a particular location data object may describe the measure of location of placement of a badge reader device. As yet another example, a particular location data object may describe the measure of location of placement of a Bluetooth sensor device. As a further example, a particular location data object may describe the measure of location of placement of a camera device. Examples of location measures described by location data object include absolute location measures (e.g., absolute location measures described in accordance with the Global Positioning System (GPS)) as well as relative location measures (e.g., relative location measures that describe the location of a particular presence-detecting sensor device with respect to the locations of one or more other presence-detecting sensor devices).

As further described above, presence-detecting sensor devices may describe an electronic device that is configured to detect the presence of an end-user and/or the presence of an end-user device within a locational proximity of the presence-detecting sensor device. Examples of presence-detecting sensor devices include Wi-Fi devices, badge reader devices, Bluetooth sensor devices, camera devices, voice detection devices, and/or the like. As described above, presence-detecting sensor devices may be configured to generate location data objects. In some embodiments, when combined, location data objects may be used to generate a traversal network.

At step/operation 1202, the predictive data analysis computing entity 106 generates a traversal network based at least in part on the location data objects. In some embodiments, the predictive data analysis computing entity 106 combines the locational information inferred based at least in part on the location data objects to generate the traversal network. A traversal network may describe one or more locations described by one or more location data objects as well as detected/assumed/given paths between pairs of the noted locations. The traversal network may, in some embodiments, be a graph data object that describes the locations as tracked location nodes and paths between pairs of locations as traversal edges. Because locations described by a traversal network are determined based at least in part on locational information provided by location data objects, and because location data objects are generated by presence-detecting sensor devices, the tracked location nodes of the traversal network describing the locations are in turn associated with the presence-detecting sensor devices, such that every tracked location node describes a location of a monitored environment, where presence of end-users and/or end-user devices within a positional proximity of the noted monitored environment is being monitored by a respective presence-detecting sensor device.

At step/operation 1203, the predictive data analysis computing entity 106 identifies one or more candidate traversal paths for a traversal agent data object. For example, the predictive data analysis computing entity 106 may generate one or more candidate traversal paths for a traversal agent data object that is associated with a healthcare worker in a healthcare facility. As another example, the predictive data analysis computing entity 106 may generate one or more candidate traversal paths for a traversal agent that object that is associated with a patient in a healthcare facility.

As described above, a traversal agent data object describes an agent (e.g., a person such as a patient or a healthcare worker, a bed carrying a person, and/or the like) that intends to travel from a first location within a physical environment of a traversal network to a second location within a physical environment of the traversal network. In some embodiments, the traversal agent data object is associated with a current location that is associated with a source node of the tracked location nodes of the noted traversal network.

As further described above, a candidate traversal path may describe a sequence of tracked location nodes in a traversal network along with a timestamp for each tracked location node in the sequence. For example, a candidate traversal path may describe a proposed path that a healthcare worker may take to reach a target destination. As another example, a candidate traversal path may describe a proposed route for carrying a patient bed to a target destination such as a surgery room, a medical imaging facility room, and/or the like. As previously noted, each tracked location node described by a candidate traversal path is associated with a timestamp, where the timestamp may be determined based at least in part on a measure of temporality that is common across all candidate traversal paths, such that the timestamps can be used to determine predicted infectious encounters between a candidate traversal path and one or more other infectious traversal paths. A candidate traversal path may thus be associated with one or more node visitation recommendations, where each node visitation recommendation describes a proposed visitation of a tracked location node at a corresponding timestamp as recommended by the candidate traversal path.

In some embodiments, to generate a candidate traversal path for a traversal agent data object, the predictive data analysis computing entity 106 identifies a source node within the tracked location nodes of the traversal network that describes a current location of the traversal agent data object, as well as a destination node within the tracked location nodes of the traversal network that describes a destination location of the traversal agent data object. For example, the source node may describe a current location of a patient bed, while the destination node may describe a surgery room to which the patient bed should be transported. In some of the noted embodiments, the predictive data analysis computing entity 106 generates the candidate traversal path as a path that connects the source node and the destination node via one or more traversal edges.

At step/operation 1204, the predictive data analysis computing entity 106 determines a predicted infectious encounter profile for each candidate traversal path, where the predicted infectious encounter profile describes one or more predicted infectious encounters for the traversal agent data object that is associated with the corresponding candidate traversal path. In some embodiments, the predictive data analysis computing entity 106 generates the predicted infectious encounter profile based at least in part on at least one of one or more infectious traversal paths or one or more infectious region designations.

As described above, a predicted infectious encounter profile for a traversal path describes a subset of the node visitation recommendations described by a corresponding candidate traversal path that is predicted to cause likely exposure to an infection. For example, the predicted infectious encounter profile may describe a subset of the node visitation recommendations described by a corresponding candidate traversal path, where each node visitation recommendation in the subset proposes visiting particular tracked location nodes at timestamps that are deemed to be within defined temporal proximity regions of infectious visitation timestamps by traversal agent data objects deemed to be infected. As another example, the predicted infectious encounter profile may describe a subset of the node visitation recommendations described by a corresponding candidate traversal path, where each node visitation recommendation in the subset proposes visiting particular tracked location nodes that are deemed to be at all times infectious or at timestamps deemed to be within a defined temporal proximity region of the timestamp of the node visitation recommendation in the subset.

As further described above, a predicted infectious encounter may describe a node visitation recommendation that is deemed to cause likely exposure to an infection based at least in part on the tracked location node of the node visitation recommendation and the timestamp of the node visitation recommendation. For example, a predicted infectious encounter may describe a node visitation recommendation that proposes visiting a tracked location node at a first time, where the first time is within a temporal proximity region of a second time associated with visitation of the particular tracked location node by an infectious individual. As another example, a predicted infectious encounter may describe a node visitation recommendation that proposes visiting a tracked location node that is deemed to be infectious at all times, such as infection hub including a cafeteria, an intensive care unit (ICU), and/or the like. As yet another example, a predicted infectious encounter may describe a node visitation recommendation that proposes visiting a tracked location node that is deemed to be infectious at particular times, where the particular times are within a temporal proximity region of the timestamp of the noted node visitation recommendation.

At step/operation 1205, the predictive data analysis computing entity 106 generates a path risk score for each candidate traversal path. In some embodiments, the predictive data analysis computing entity 106 generates the path risk score based at least in part on each predicted total VPI measure associated with a predicted infectious encounter for the candidate traversal path. In some embodiments, to generate the predicted risk score for a candidate traversal path, the predictive data analysis computing entity 106 generates a predicted VPI measure for each predicted infectious encounter that is deemed to be associated with the candidate traversal path based at least in part on the cross-node infectious encounter profile for the candidate traversal path. A predicted VPI measure may describe an estimated/predicted quantity of infectious/viral particles inhaled by a person described by a traversal agent data object when the person faces the circumstances described by a corresponding predicted infectious encounter. In some embodiments, a predicted VPI measure is determined based at least in part on a predicted respiration rate measure for the traversal agent data object, a predicted tidal volume measure for the traversal agent data object, and a predicted cumulative VPD measure for the traversal agent data object across a predicted length of the corresponding predicted infectious encounter. In some embodiments, the predicted VPI measure is determined in accordance with the equation $VPI_{Total} = RR \times TV \times \Sigma_{t=1}^{T} VPD_t$, where $VPI_{Total}$ is the predicted total VPI measure, RR is the predicted respiration rate measure, TV is the predicted tidal volume measure, and $\Sigma_{t=1}^{T} VPD_t$ is the predicted total VPD measure.

At step/operation 1206, the predictive data analysis computing entity 106 generates a length measure for each candidate traversal path. In some embodiments, the predictive data analysis computing entity 106 combines edge-level length data for each edge traversal associated with a candidate traversal path to determine a candidate traversal path for the candidate traversal path. In some embodiments, the predictive data analysis computing entity 106 combines edge-level length data for each edge traversal associated with a candidate traversal path as well as node-level length data for each node traversal associated with a candidate traversal path to determine a candidate traversal path for the candidate traversal path.

Figure 10:
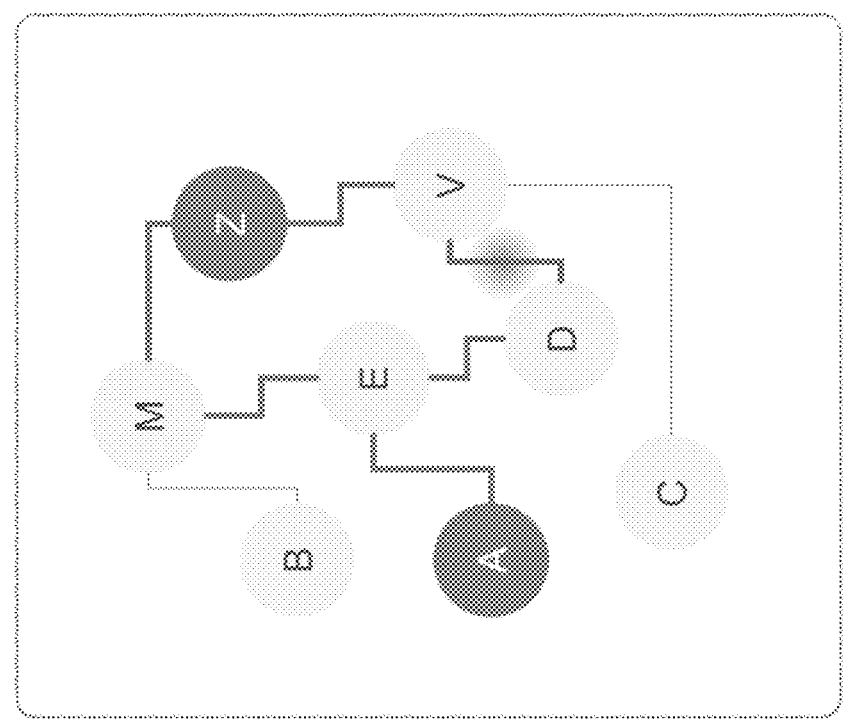

At step/operation 1207, the predictive data analysis computing entity 106 causes display of a prediction output user interface that enables viewing the relative path risk scores and the relative length measures across the candidate traversal paths. For example, the predictive data analysis computing entity 106 causes display of a prediction output user interface that enables ranking candidate traversal paths based at least in part on at least one of relative path risk scores and the relative length measures across the candidate traversal paths. In some embodiments, the predictive data analysis computing entity 106 causes display of a prediction output user interface that displays all candidate traversal paths in accordance with a graphical user interface element depicting the traversal network, where candidate traversal paths are marked on the graphical user interface element along with a measure of the path risk score of the noted paths. An operational example of such a prediction output user interface 1000 is depicted in FIG. 10.

At step/operation 1208, the predictive data analysis computing entity 106 receives a user interaction with the prediction output user interface that selects a candidate traversal path among the group of candidate traversal paths depicted by the prediction output user interface. In some embodiments, the prediction output user interface is displayed by an external computing entity 102, and the external computing entity 102 is configured to record the user interaction and transmit the user interaction to the predictive data analysis computing entity 106.

At step/operation 1209, the predictive data analysis computing entity 106 sets access parameters for one or more areas (e.g., rooms, hallways, and/or the like) within a building associated with the traversal network in accordance with the selected candidate traversal path. In some embodiments, the predictive data analysis computing entity 106 sets the access parameters by performing at least one of the following: (i) communicating with one or more networked locks associated with the building, and (ii) communicating with a networked device that controls the configuration of one or more locks associated with the building.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
receiving, by one or more processors and using a presence-detecting sensor positioned within a monitored area of a plurality of monitored areas of a building, a location data object for the monitored area, wherein the location data object comprises a device location field that identifies the monitored area, a creation time stamp, and a validity duration that identifies a valid time period from the creation time stamp;
generating, by the one or more processors, a traversal network for the building based on a combination of a plurality of location data objects that comprise the location data object, wherein (i) the traversal network comprises a graph data object that defines a plurality of tracked location nodes respectively corresponding to a plurality of presence-detecting sensors positioned within the plurality of monitored areas of the building, (ii) the plurality of tracked location nodes comprise (a) a first tracked location node that is deemed infectious at all times, and (b) a second tracked location node that is deemed infectious within a temporal proximity region that is based at least in part on the creation time stamp and the validity duration of the location data object;
identifying, by the one or more processors, a candidate traversal path from a plurality of candidate traversal paths within the traversal network, wherein (i) the candidate traversal path comprises a linked list of node visitation recommendations and (ii) a node visitation recommendation of the linked list of node visitation recommendations is indicative of (a) the second tracked location node of the traversal network and (b) a proposed visitation timestamp indicative of a proposed visitation time at the second tracked location node;

determining, by the one or more processors, a cross-node infectious encounter profile for the candidate traversal path that is indicative of a predicted infectious encounter for a traversal agent data object, wherein:
(i) the predicted infectious encounter corresponds to the node visitation recommendation, and
(ii) the predicted infectious encounter is based at least in part on (a) the proposed visitation timestamp and (b) the temporal proximity region;

determining, by the one or more processors, an optimal traversal path from the plurality of candidate traversal paths based at least in part on the cross-node infectious encounter profile; and controlling, by the one or more processors and using one or more networked devices, a physical configuration of a lock associated with the building to control access to one or more of the plurality of monitored areas of the building in accordance with the optimal traversal path.

2. The computer-implemented method of claim 1, further comprising:
determining a predicted total viral particle inhalation (VPI) measure for the predicted infectious encounter based at least in part on the cross-node infectious encounter profile, wherein the predicted total VPI measure is based at least in part on:
a predicted respiration rate measure for the traversal agent data object,
a predicted tidal volume measure for the traversal agent data object, and
a predicted cumulative viral particle density (VPD) measure for the traversal agent data object across a predicted length of the predicted infectious encounter.

3. The computer-implemented method of claim 2, wherein the predicted cumulative VPD measure is determined by combining one or more per-time-unit predicted VPD measures for one or more time units of the predicted length of the predicted infectious encounter.

4. The computer-implemented method of claim 3, wherein:
a per-time-unit predicted VPD measure for a time unit of the one or more time units is determined based at least in part on a total predicted viral particle release (VPR) measure by an infectious individual up to the time unit and a room volume measure for the monitored area, and
the total predicted VPR measure is associated with one or more infectious traversal agent data objects.

5. The computer-implemented method of claim 1, wherein identifying the candidate traversal path from the plurality of candidate traversal paths comprises:
identifying a subset of the plurality of tracked location nodes and a plurality of traversal edges of the traversal network,
identifying a source node and a destination node of the subset of the plurality of tracked location nodes, and
generating the plurality of candidate traversal paths based at least in part on the source node, the destination node, and the plurality of traversal edges.

6. The computer-implemented method of claim 1, wherein the optimal traversal path is based at least in part on a plurality of path length measures for the plurality of candidate traversal paths.

7. A system comprising memory and one or more processors communicatively coupled to the memory, the one or more processors configured to:

receive, using a presence-detecting sensor positioned within a monitored area of a plurality of monitored areas of a building, a location data object for the monitored area, wherein the location data object comprises a device location field that identifies the monitored area, a creation time stamp, and a validity duration that identifies a valid time period from the creation time stamp;

generate a traversal network for the building based on a combination of a plurality of location data objects that comprise the location data object, wherein (i) the traversal network comprises a graph data object that defines a plurality of tracked location nodes respectively corresponding to a plurality of presence-detecting sensors positioned within the plurality of monitored areas of the building, (ii) the plurality of tracked location nodes comprise (a) a first tracked location node that is deemed infectious at all times, and (b) a second tracked location node that is deemed infectious within a temporal proximity region that is based at least in part on the creation time stamp and the validity duration of the location data object;

identify a candidate traversal path from a plurality of candidate traversal paths within the traversal network, wherein (i) the candidate traversal path comprises a linked list of node visitation recommendations and (ii) a node visitation recommendation of the linked list of node visitation recommendations is indicative of (a) the second tracked location node of the traversal network and (b) a proposed visitation timestamp indicative of a proposed visitation time at the second tracked location node;

determine a cross-node infectious encounter profile for the candidate traversal path that is indicative of a predicted infectious encounter for a traversal agent data object, wherein:
(i) the predicted infectious encounter corresponds to the node visitation recommendation, and
(ii) the predicted infectious encounter is based at least in part on (a) the proposed visitation timestamp and (b) the temporal proximity region;

determine an optimal traversal path from the plurality of candidate traversal paths based at least in part on the cross-node infectious encounter profile; and control, using one or more networked devices, a physical configuration of a lock associated with the building to control access to one or more of the plurality of monitored areas of the building in accordance with the optimal traversal path.

8. The system of claim 7, wherein the one or more processors are further configured to:
determine a predicted total viral particle inhalation (VPI) measure for the predicted infectious encounter based at least in part on the cross-node infectious encounter profile, wherein the predicted total VPI measure is based at least in part on:
a predicted respiration rate measure for the traversal agent data object,
a predicted tidal volume measure for the traversal agent data object, and
a predicted cumulative viral particle density (VPD) measure for the traversal agent data object across a predicted length of the predicted infectious encounter.

9. The system of claim 8, wherein the predicted cumulative VPD measure is determined by combining one or more per-time-unit predicted VPD measures for one or more time units of the predicted length of the predicted infectious encounter.

10. The system of claim 9, wherein:
a per-time-unit predicted VPD measure for a time unit of the one or more time units is determined based at least in part on a total predicted viral particle release (VPR) measure by an infectious individual up to the time unit and a room volume measure for the monitored area, and the total predicted VPR measure is associated with one or more infectious traversal agent data objects.

11. The computing system of claim 7, wherein identifying the candidate traversal path from the plurality of candidate traversal paths comprises:
identifying a subset of the plurality of tracked location nodes and a plurality of traversal edges of the traversal network,
identifying a source node and a destination node of the subset of the plurality of tracked location nodes, and
generating the plurality of candidate traversal paths based at least in part on the source node, the destination node, and the plurality of traversal edges.

12. The system of claim 7, wherein the optimal traversal path is based at least in part on a plurality of path length measures for the plurality of candidate traversal paths.

13. One or more non-transitory computer-readable storage media including instructions that, when executed by one or more processors, cause the one or more processors to:
receive, using a presence-detecting sensor positioned within a monitored area of a plurality of monitored areas of a building, a location data object for the monitored area, wherein the location data object comprises a device location field that identifies the monitored area, a creation time stamp, and a validity duration that identifies a valid time period from the creation time stamp;
generate a traversal network for the building based on a combination of a plurality of location data objects that comprise the location data object, wherein (i) the traversal network comprises a graph data object that defines a plurality of tracked location nodes respectively corresponding to a plurality of presence-detecting sensors positioned within the plurality of monitored areas of the building, (ii) the plurality of tracked location nodes comprise (a) a first tracked location node that is deemed infectious at all times, and (b) a second tracked location node that is deemed infectious within a temporal proximity region that is based at least in part on the creation time stamp and the validity duration of the location data object;
identify a candidate traversal path from a plurality of candidate traversal paths within the traversal network, wherein (i) the candidate traversal path comprises a linked list of node visitation recommendations and (ii) a node visitation recommendation of the linked list of node visitation recommendations is indicative of (a) the second tracked location node of the traversal network and (b) a proposed visitation timestamp indicative of a proposed visitation time at the second tracked location node;
determine a cross-node infectious encounter profile for the candidate traversal path that is indicative of a predicted infectious encounter for a traversal agent data object, wherein:
(i) the predicted infectious encounter corresponds to the node visitation recommendation, and
(ii) the predicted infectious encounter is based at least in part on (a) the proposed visitation timestamp and (b) the temporal proximity region;
determine an optimal traversal path from the plurality of candidate traversal paths based at least in part on the cross-node infectious encounter profile; and
control, using one or more networked devices, a physical configuration of a lock associated with the building to control access to one or more of the plurality of monitored areas of the building in accordance with the optimal traversal path.

14. The one or more non-transitory computer-readable storage media of claim 13, wherein the one or more processors are further caused to:
determine a predicted total viral particle inhalation (VPI) measure for the predicted infectious encounter based at least in part on the cross-node infectious encounter profile, wherein the predicted total VPI measure is based at least in part on:
a predicted respiration rate measure for the traversal agent data object,
a predicted tidal volume measure for the traversal agent data object, and
a predicted cumulative viral particle density (VPD) measure for the traversal agent data object across a predicted length of the predicted infectious encounter.

15. The one or more non-transitory computer-readable storage media of claim 14, wherein the predicted cumulative VPD measure is determined by combining one or more per-time-unit predicted VPD measures for one or more time units of the predicted length of the predicted infectious encounter.

16. The one or more non-transitory computer-readable storage media of claim 13, wherein identifying the candidate traversal path from the plurality of candidate traversal paths comprises:
identifying a subset of the plurality of tracked location nodes and the plurality of traversal edges of the traversal network,
identifying a source node and a destination node of the subset of the plurality of tracked location nodes, and
generating the plurality of candidate traversal paths based at least in part on the source node, the destination node, and the plurality of traversal edges.

* * * * *

UNITED STATES PATENT AND TRADEMARK OFFICE
CERTIFICATE OF CORRECTION

Page 1 of 3

PATENT NO. : 12,249,431 B2
APPLICATION NO. : 17/110965
DATED : March 11, 2025
INVENTOR(S) : Vicente Rubén Del Pino Ruiz et al.

It is certified that error appears in the above-identified patent and that said Letters Patent is hereby corrected as shown below:

In the Drawings

In Sheet 10 of 13, replace FIG. 9 with replacement Fig. 9 therefor, as shown on the attached drawing sheet.

In Sheet 13 of 13, replace FIG. 9 with original Fig. 12 therefor, as shown on the attached drawing sheet.

In the Claims

In Column 29, Line 12, Claim 11, delete "computing system" and insert -- system --, therefor.

Signed and Sealed this
Third Day of June, 2025

Coke Morgan Stewart
*Acting Director of the United States Patent and Trademark Office*